(12) United States Patent
Chabriere et al.

(10) Patent No.: US 9,492,501 B2
(45) Date of Patent: Nov. 15, 2016

(54) ANTIVIRAL AGENT

(75) Inventors: Eric Chabriere, Marseilles (FR); Mikael Elias, Florange (FR); Olivier Rohr, Miserey-Salines (FR); Christian Schwartz, Lingolsheim (FR)

(73) Assignees: CENTRE NATIONAL DE LA RECHERCHE SCIENTIFIQUE, Paris (FR); UNIVERSITE DE STRASBOURG, Strasbourg (FR); UNIVERSITE DE LA MEDITERRANEE, Marseilles (FR)

( * ) Notice: Subject to any disclaimer, the term of this patent is extended or adjusted under 35 U.S.C. 154(b) by 1342 days.

(21) Appl. No.: 13/254,502

(22) PCT Filed: Mar. 4, 2010

(86) PCT No.: PCT/FR2010/050369
§ 371 (c)(1),
(2), (4) Date: Oct. 14, 2011

(87) PCT Pub. No.: WO2010/100381
PCT Pub. Date: Sep. 10, 2010

(65) Prior Publication Data
US 2012/0035098 A1 Feb. 9, 2012

(30) Foreign Application Priority Data

Mar. 4, 2009 (FR) .................................. 09 51347

(51) Int. Cl.
*C07K 14/435* (2006.01)
*A61K 38/17* (2006.01)
*A61K 45/06* (2006.01)
*G01N 33/569* (2006.01)

(52) U.S. Cl.
CPC ............ *A61K 38/1709* (2013.01); *A61K 45/06* (2013.01); *G01N 33/56983* (2013.01); *G01N 33/56988* (2013.01)

(58) Field of Classification Search
CPC ......................... C07K 14/435; A61K 38/1709
USPC ......................................................... 530/350
See application file for complete search history.

(56) References Cited

U.S. PATENT DOCUMENTS

2007/0196879 A1    8/2007   Chabriere et al.

FOREIGN PATENT DOCUMENTS

FR          2 861 731 A1    5/2005

OTHER PUBLICATIONS

Darbinian-Sarkissian N et al: "p27(SJ), a novel protein in St John's Wort, that suppresses expression of HIV-I genome", Gene Therapy, vol. 13, No. 4, Feb. 2006, pp. 288-295, XP002561014.
Perera et al: II Proteins related to St. John's Wort p27<SJ>, a suppressor of HIV-1 expression, are ubiquitous in plants, Phytochemistry, Pergamon Press, GB, vol. 69, No. 4, Nov. 19, 2007, pp. 865-872, XP022473168.
Morales R et al: "Serendipitous Discovery and X-Ray Structure of a Human Phosphate Binding Apolipoprotein", Structure, Current Biology Ltd., Philadelphia, PA, US, vol. 14, No. 3, Mar. 1, 2006, pp. 601-609, XP025134109.
International Search Report, dated Apr. 19, 2011, in Application No. PCT/FR2010/050369.

*Primary Examiner* — David Lukton
(74) *Attorney, Agent, or Firm* — Young & Thompson

(57) ABSTRACT

The present invention describes the use of a composition including or constituted by at least one element chosen from:
  a specific protein including or consisting of the amino acid sequence SEQ ID NO: 5, and
  a protein homologous to the specific protein,
for the preparation of a medicament intended for the prevention or treatment of pathologies associated with a viral infection or an inflammation.

13 Claims, 7 Drawing Sheets

HPBP

TAT

SEQUENCE LISTING

```
<160> NUMBER OF SEQ ID NOS: 10

<210> SEQ ID NO 1
<211> LENGTH: 376
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D ou S
<220> FEATURE:
<221> NAME/KEY: MISC_FEATURE
<222> LOCATION: (3)..(3)
<223> OTHER INFORMATION: N ou D
<220> FEATURE:
<221> NAME/KEY: MISC_FEATURE
<222> LOCATION: (11)..(11)
<223> OTHER INFORMATION: Q ou E
<220> FEATURE:
<221> NAME/KEY: MISC_FEATURE
<222> LOCATION: (30)..(30)
<223> OTHER INFORMATION: V ou T
<220> FEATURE:
<221> NAME/KEY: MISC_FEATURE
<222> LOCATION: (43)..(43)
<223> OTHER INFORMATION: K ou S
<220> FEATURE:
<221> NAME/KEY: MISC_FEATURE
<222> LOCATION: (50)..(50)
<223> OTHER INFORMATION: D ou N
<220> FEATURE:
<221> NAME/KEY: MISC_FEATURE
<222> LOCATION: (54)..(54)
<223> OTHER INFORMATION: N ou D
<220> FEATURE:
<221> NAME/KEY: MISC_FEATURE
<222> LOCATION: (67)..(67)
<223> OTHER INFORMATION: T ou S
<220> FEATURE:
<221> NAME/KEY: MISC_FEATURE
<222> LOCATION: (68)..(68)
<223> OTHER INFORMATION: E ou Q
<220> FEATURE:
```

<220> FEATURE:
<221> NAME/KEY: MISC_FEATURE
<222> LOCATION: (75)..(75)
<223> OTHER INFORMATION: D ou N
<220> FEATURE:
<221> NAME/KEY: MISC_FEATURE
<222> LOCATION: (77)..(77)
<223> OTHER INFORMATION: E ou Q
<220> FEATURE:
<221> NAME/KEY: MISC_FEATURE
<222> LOCATION: (85)..(85)
<223> OTHER INFORMATION: Q ou E
<220> FEATURE:
<221> NAME/KEY: MISC_FEATURE
<222> LOCATION: (102)..(102)
<223> OTHER INFORMATION: A ou G
<220> FEATURE:
<221> NAME/KEY: MISC_FEATURE
<222> LOCATION: (122)..(122)
<223> OTHER INFORMATION: D ou N
<220> FEATURE:
<221> NAME/KEY: MISC_FEATURE
<222> LOCATION: (143)..(143)
<223> OTHER INFORMATION: S ou V
<220> FEATURE:
<221> NAME/KEY: MISC_FEATURE
<222> LOCATION: (219)..(219)
<223> OTHER INFORMATION: T ou S
<220> FEATURE:
<221> NAME/KEY: MISC_FEATURE
<222> LOCATION: (224)..(224)
<223> OTHER INFORMATION: D ou N
<220> FEATURE:
<221> NAME/KEY: MISC_FEATURE
<222> LOCATION: (252)..(252)
<223> OTHER INFORMATION: V ou S
<220> FEATURE:
<221> NAME/KEY: MISC_FEATURE
<222> LOCATION: (266)..(266)
<223> OTHER INFORMATION: D ou N

<400> SEQUENCE: 1

Xaa Ile Xaa Gly Gly Gly Ala Thr Leu Pro Xaa Lys Leu Tyr Leu Thr
1               5                   10                  15

Pro Asp Val Leu Thr Ala Gly Phe Ala Pro Tyr Ile Gly Xaa Gly Ser
            20                  25                  30

Gly Lys Gly Lys Ile Ala Phe Leu Glu Asn Xaa Tyr Asn Gln Phe Gly
        35                  40                  45

Thr Xaa Thr Thr Lys Xaa Val His Trp Ala Gly Ser Asp Ser Lys Leu
50                  55                  60

Thr Ala Xaa Xaa Leu Ala Thr Tyr Ala Ala Xaa Lys Xaa Pro Gly Trp
65                  70                  75                  80

Gly Lys Leu Ile Xaa Val Pro Ser Val Ala Thr Ser Val Ala Ile Pro
            85                  90                  95

Phe Arg Lys Ala Gly Xaa Asn Ala Val Asp Leu Ser Val Lys Glu Leu
            100                 105                 110

Cys Gly Val Phe Ser Gly Arg Ile Ala Xaa Trp Ser Gly Ile Thr Gly
            115                 120                 125

Ala Gly Arg Ser Gly Pro Ile Gln Val Val Tyr Arg Ala Glu Xaa Ser
            130                 135                 140

Gly Thr Thr Glu Leu Phe Thr Arg Phe Leu Asn Ala Lys Cys Thr Thr
145                 150                 155                 160

Gln Pro Gly Thr Phe Ala Val Thr Thr Val Phe Ala Asn Ser Tyr Ser
                165                 170                 175

Leu Gly Leu Ser Pro Leu Ala Gly Ala Val Ala Ala Ile Gly Ser Val
            180                 185                 190

Gly Val Met Ala Ala Asp Asn Asp Val Thr Thr Ala Gln Gly Arg Ile

```
                195                 200                 205
Thr Tyr Ile Ser Pro Asp Phe Ala Ala Pro Xaa Leu Ala Gly Leu Xaa
210                 215                 220

Asp Ala Thr Lys Val Ala Arg Thr Gly Lys Gly Ser Ser Gly Gly
225                 230                 235                 240

Gly Ala Glu Gly Lys Ser Pro Ala Ala Asn Xaa Ser Ala Ala Ile
                245                 250                 255

Ser Val Val Pro Leu Pro Ala Ala Xaa Arg Gly Asp Pro Asn Val
                260                 265                 270

Trp Thr Pro Val Phe Gly Ala Val Thr Gly Gly Val Val Ala Tyr
                275                 280                 285

Pro Asp Ser Gly Tyr Pro Ile Leu Gly Phe Thr Asp Leu Ile Phe Ser
290                 295                 300

Glu Cys Tyr Ala Asn Ala Thr Gln Thr Gly Gln Val Arg Asn Phe Phe
305                 310                 315                 320

Thr Lys His Tyr Gly Thr Ser Ala Asn Asp Asn Ala Ala Ile Gln Ala
                325                 330                 335

Asn Ala Phe Val Pro Leu Pro Ser Asn Trp Lys Ala Ala Val Arg Ala
                340                 345                 350

Ser Tyr Leu Thr Ala Ser Asn Ala Leu Ser Ile Gly Asp Ser Ala Val
                355                 360                 365

Cys Gly Gly Lys Gly Arg Pro Glu
370                 375

<210> SEQ ID NO 2
<211> LENGTH: 376
<212> TYPE: PRT
<213> ORGANISM: Homo sapiens

<400> SEQUENCE: 2

Asp Ile Asn Gly Gly Gly Ala Thr Leu Pro Gln Lys Leu Tyr Leu Thr
1               5                   10                  15

Pro Asp Val Leu Thr Ala Gly Phe Ala Pro Tyr Ile Gly Val Gly Ser
                20                  25                  30

Gly Lys Gly Lys Ile Ala Phe Leu Glu Asn Lys Tyr Asn Gln Phe Gly
            35                  40                  45

Thr Asp Thr Thr Lys Asn Val His Trp Ala Gly Ser Asp Ser Lys Leu
50                  55                  60

Thr Ala Thr Glu Leu Ala Thr Tyr Ala Ala Asp Lys Glu Pro Gly Trp
65                  70                  75                  80

Gly Lys Leu Ile Gln Val Pro Ser Val Ala Thr Ser Val Ala Ile Pro
                85                  90                  95

Phe Arg Lys Ala Gly Ala Asn Ala Val Asp Leu Ser Val Lys Glu Leu
            100                 105                 110

Cys Gly Val Phe Ser Gly Arg Ile Ala Asp Trp Ser Gly Ile Thr Gly
        115                 120                 125

Ala Gly Arg Ser Gly Pro Ile Gln Val Val Tyr Arg Ala Glu Ser Ser
    130                 135                 140

Gly Thr Thr Glu Leu Phe Thr Arg Phe Leu Asn Ala Lys Cys Thr Thr
145                 150                 155                 160

Gln Pro Gly Thr Phe Ala Val Thr Thr Val Phe Ala Asn Ser Tyr Ser
                165                 170                 175

Leu Gly Leu Ser Pro Leu Ala Gly Ala Val Ala Ala Ile Gly Ser Val
                180                 185                 190
```

```
Gly Val Met Ala Ala Asp Asn Asp Val Thr Thr Ala Gln Gly Arg Ile
            195                 200                 205

Thr Tyr Ile Ser Pro Asp Phe Ala Ala Pro Thr Leu Ala Gly Leu Asp
        210                 215                 220

Asp Ala Thr Lys Val Ala Arg Thr Gly Lys Gly Ser Ser Ser Gly Gly
225                 230                 235                 240

Gly Ala Glu Gly Lys Ser Pro Ala Ala Asn Val Ser Ala Ala Ile
            245                 250                 255

Ser Val Val Pro Leu Pro Ala Ala Asp Arg Gly Asp Pro Asn Val
            260                 265                 270

Trp Thr Pro Val Phe Gly Ala Val Thr Gly Gly Val Val Ala Tyr
            275                 280                 285

Pro Asp Ser Gly Tyr Pro Ile Leu Gly Phe Thr Asp Leu Ile Phe Ser
        290                 295                 300

Glu Cys Tyr Ala Asn Ala Thr Gln Thr Gly Gln Val Arg Asn Phe Phe
305                 310                 315                 320

Thr Lys His Tyr Gly Thr Ser Ala Asn Asp Asn Ala Ala Ile Gln Ala
                325                 330                 335

Asn Ala Phe Val Pro Leu Pro Ser Asn Trp Lys Ala Ala Val Arg Ala
            340                 345                 350

Ser Tyr Leu Thr Ala Ser Asn Ala Leu Ser Ile Gly Asp Ser Ala Val
            355                 360                 365

Cys Gly Gly Lys Gly Arg Pro Glu
            370                 375

<210> SEQ ID NO 3
<211> LENGTH: 376
<212> TYPE: PRT
<213> ORGANISM: Homo sapiens

<400> SEQUENCE: 3

Ser Ile Asp Gly Gly Gly Ala Thr Leu Pro Glu Lys Leu Tyr Leu Thr
1               5                   10                  15

Pro Asp Val Leu Thr Ala Gly Phe Ala Pro Tyr Ile Gly Thr Gly Ser
            20                  25                  30

Gly Lys Gly Lys Ile Ala Phe Leu Glu Asn Ser Tyr Asn Gln Phe Gly
        35                  40                  45

Thr Asn Thr Thr Lys Asp Val His Trp Ala Gly Ser Asp Ser Lys Leu
50                  55                  60

Thr Ala Ser Gln Leu Ala Thr Tyr Ala Ala Asn Lys Gln Pro Gly Trp
65                  70                  75                  80

Gly Lys Leu Ile Glu Val Pro Ser Val Ala Thr Ser Val Ala Ile Pro
                85                  90                  95

Phe Arg Lys Ala Gly Gly Asn Ala Val Asp Leu Ser Val Lys Glu Leu
            100                 105                 110

Cys Gly Val Phe Ser Gly Arg Ile Ala Asn Trp Ser Gly Ile Thr Gly
        115                 120                 125

Ala Gly Arg Ser Gly Pro Ile Gln Val Val Tyr Arg Ala Glu Val Ser
    130                 135                 140

Gly Thr Thr Glu Leu Phe Thr Arg Phe Leu Asn Ala Lys Cys Thr Thr
145                 150                 155                 160

Gln Pro Gly Thr Phe Ala Val Thr Thr Val Phe Ala Asn Ser Tyr Ser
                165                 170                 175

Leu Gly Leu Ser Pro Leu Ala Gly Ala Val Ala Ala Ile Gly Ser Val
            180                 185                 190
```

Gly Val Met Ala Ala Asp Asn Asp Val Thr Thr Ala Gln Gly Arg Ile
            195                 200                 205

Thr Tyr Ile Ser Pro Asp Phe Ala Ala Pro Ser Leu Ala Gly Leu Asn
        210                 215                 220

Asp Ala Thr Lys Val Ala Arg Thr Gly Lys Gly Ser Ser Ser Gly Gly
225                 230                 235                 240

Gly Ala Glu Gly Lys Ser Pro Ala Ala Asn Ser Ser Ala Ala Ile
                245                 250                 255

Ser Val Val Pro Leu Pro Ala Ala Asn Arg Gly Asp Pro Asn Val
                260                 265                 270

Trp Thr Pro Val Phe Gly Ala Val Thr Gly Gly Val Val Ala Tyr
                275                 280                 285

Pro Asp Ser Gly Tyr Pro Ile Leu Gly Phe Thr Asp Leu Ile Phe Ser
        290                 295                 300

Glu Cys Tyr Ala Asn Ala Thr Gln Thr Gly Gln Val Arg Asn Phe Phe
305                 310                 315                 320

Thr Lys His Tyr Gly Thr Ser Ala Asn Asp Asn Ala Ala Ile Gln Ala
                325                 330                 335

Asn Ala Phe Val Pro Leu Pro Ser Asn Trp Lys Ala Ala Val Arg Ala
                340                 345                 350

Ser Tyr Leu Thr Ala Ser Asn Ala Leu Ser Ile Gly Asp Ser Ala Val
                355                 360                 365

Cys Gly Gly Lys Gly Arg Pro Glu
                370                 375

<210> SEQ ID NO 4
<211> LENGTH: 263
<212> TYPE: PRT
<213> ORGANISM: Hypericum perforatum

<400> SEQUENCE: 4

Met Ala Asp Ile Asn Gly Gly Gly Ala Thr Leu Pro Gln Ala Leu Tyr
1               5                   10                  15

Gln Thr Ser Gly Val Leu Thr Ala Gly Phe Ala Pro Tyr Ile Gly Val
                20                  25                  30

Gly Ser Gly Asn Gly Lys Ala Ala Phe Leu Asn Asn Asp Tyr Thr Lys
            35                  40                  45

Phe Gln Ala Gly Val Thr Asn Lys Asn Val His Trp Ala Gly Ser Asp
        50                  55                  60

Ser Lys Leu Ser Ala Thr Glu Leu Ser Thr Tyr Ala Ser Ala Lys Gln
65                  70                  75                  80

Pro Thr Trp Gly Lys Leu Ile Gln Val Pro Ser Val Gly Thr Ala Val
                85                  90                  95

Ala Ile Pro Phe Asn Lys Ser Gly Thr Ala Ala Val Asp Leu Ser Val
            100                 105                 110

Ser Glu Leu Cys Gly Val Phe Ser Gly Arg Ile Thr Asp Trp Ser Gly
        115                 120                 125

Ile Ser Gly Ser Gly Arg Thr Gly Ala Ile Thr Val Val Tyr Arg Ser
    130                 135                 140

Glu Ser Ser Gly Thr Thr Glu Leu Phe Thr Arg Phe Leu Asn Ala Lys
145                 150                 155                 160

Cys Ala Glu Thr Gly Thr Phe Asn Ile Ser Thr Thr Phe Gly Thr Ser
                165                 170                 175

Tyr Thr Gly Gly Leu Pro Ala Gly Ala Val Ser Ala Ala Gly Ser Gln

```
                180             185             190
Gly Val Met Thr Ala Leu Ala Gly Ala Asp Gly Gly Thr Thr Tyr Met
            195                 200                 205

Ser Pro Asp Phe Ala Ala Pro Thr Leu Ala Gly Leu Asp Asp Ala Thr
        210                 215                 220

Lys Val Ala Arg Val Gly Lys Asp Val Ala Thr Asn Thr Ala Gly Val
225                 230                 235                 240

Ser Pro Ala Ala Ala Asn Val Ser Ala Ala Ile Asn Ala Val Pro Val
                245                 250                 255

Pro Ala Ser Thr Glu Lys Pro
            260

<210> SEQ ID NO 5
<211> LENGTH: 50
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D ou S
<220> FEATURE:
<221> NAME/KEY: MISC_FEATURE
<222> LOCATION: (3)..(3)
<223> OTHER INFORMATION: N ou D
<220> FEATURE:
<221> NAME/KEY: MISC_FEATURE
<222> LOCATION: (11)..(11)
<223> OTHER INFORMATION: Q ou E
<220> FEATURE:
<221> NAME/KEY: MISC_FEATURE
<222> LOCATION: (30)..(30)
<223> OTHER INFORMATION: V ou T
<220> FEATURE:
<221> NAME/KEY: MISC_FEATURE
<222> LOCATION: (43)..(43)
<223> OTHER INFORMATION: K ou S
<220> FEATURE:
<221> NAME/KEY: MISC_FEATURE
<222> LOCATION: (50)..(50)
<223> OTHER INFORMATION: D ou N

<400> SEQUENCE: 5

Xaa Ile Xaa Gly Gly Gly Ala Thr Leu Pro Xaa Lys Leu Tyr Leu Thr
1               5                   10                  15

Pro Asp Val Leu Thr Ala Gly Phe Ala Pro Tyr Ile Gly Xaa Gly Ser
            20                  25                  30

Gly Lys Gly Lys Ile Ala Phe Leu Glu Asn Xaa Tyr Asn Gln Phe Gly
        35                  40                  45

Thr Xaa
    50

<210> SEQ ID NO 6
<211> LENGTH: 260
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: D ou S
<220> FEATURE:
<221> NAME/KEY: MISC_FEATURE
<222> LOCATION: (3)..(3)
<223> OTHER INFORMATION: N ou D
<220> FEATURE:
<221> NAME/KEY: MISC_FEATURE
<222> LOCATION: (11)..(11)
<223> OTHER INFORMATION: Q ou E
<220> FEATURE:
```

-continued

```
<221> NAME/KEY: MISC_FEATURE
<222> LOCATION: (30)..(30)
<223> OTHER INFORMATION: V ou T
<220> FEATURE:
<221> NAME/KEY: MISC_FEATURE
<222> LOCATION: (43)..(43)
<223> OTHER INFORMATION: K ou S
<220> FEATURE:
<221> NAME/KEY: MISC_FEATURE
<222> LOCATION: (50)..(50)
<223> OTHER INFORMATION: D ou N
<220> FEATURE:
<221> NAME/KEY: MISC_FEATURE
<222> LOCATION: (54)..(54)
<223> OTHER INFORMATION: N ou D
<220> FEATURE:
<221> NAME/KEY: MISC_FEATURE
<222> LOCATION: (67)..(67)
<223> OTHER INFORMATION: T ou S
<220> FEATURE:
<221> NAME/KEY: MISC_FEATURE
<222> LOCATION: (68)..(68)
<223> OTHER INFORMATION: E ou Q
<220> FEATURE:
<221> NAME/KEY: MISC_FEATURE
<222> LOCATION: (75)..(75)
<223> OTHER INFORMATION: D ou N
<220> FEATURE:
<221> NAME/KEY: MISC_FEATURE
<222> LOCATION: (77)..(77)
<223> OTHER INFORMATION: E ou Q
<220> FEATURE:
<221> NAME/KEY: MISC_FEATURE
<222> LOCATION: (85)..(85)
<223> OTHER INFORMATION: Q ou E
<220> FEATURE:
<221> NAME/KEY: MISC_FEATURE
<222> LOCATION: (102)..(102)
<223> OTHER INFORMATION: A ou G
<220> FEATURE:
<221> NAME/KEY: MISC_FEATURE
<222> LOCATION: (122)..(122)
<223> OTHER INFORMATION: D ou N
<220> FEATURE:
<221> NAME/KEY: MISC_FEATURE
<222> LOCATION: (143)..(143)
<223> OTHER INFORMATION: S ou V
<220> FEATURE:
<221> NAME/KEY: MISC_FEATURE
<222> LOCATION: (219)..(219)
<223> OTHER INFORMATION: T ou S
<220> FEATURE:
<221> NAME/KEY: MISC_FEATURE
<222> LOCATION: (224)..(224)
<223> OTHER INFORMATION: D ou N
<220> FEATURE:
<221> NAME/KEY: MISC_FEATURE
<222> LOCATION: (252)..(252)
<223> OTHER INFORMATION: V ou S

<400> SEQUENCE: 6

Xaa Ile Xaa Gly Gly Gly Ala Thr Leu Pro Xaa Lys Leu Tyr Leu Thr
1               5                   10                  15

Pro Asp Val Leu Thr Ala Gly Phe Ala Pro Tyr Ile Gly Xaa Gly Ser
            20                  25                  30

Gly Lys Gly Lys Ile Ala Phe Leu Glu Asn Xaa Tyr Asn Gln Phe Gly
        35                  40                  45

Thr Xaa Thr Thr Lys Xaa Val His Trp Ala Gly Ser Asp Ser Lys Leu
    50                  55                  60

Thr Ala Xaa Xaa Leu Ala Thr Tyr Ala Ala Xaa Lys Xaa Pro Gly Trp
65                  70                  75                  80

Gly Lys Leu Ile Xaa Val Pro Ser Val Ala Thr Ser Val Ala Ile Pro
            85                  90                  95
```

```
Phe Arg Lys Ala Gly Xaa Asn Ala Val Asp Leu Ser Val Lys Glu Leu
            100                 105                 110

Cys Gly Val Phe Ser Gly Arg Ile Ala Xaa Trp Ser Gly Ile Thr Gly
        115                 120                 125

Ala Gly Arg Ser Gly Pro Ile Gln Val Val Tyr Arg Ala Glu Xaa Ser
    130                 135                 140

Gly Thr Thr Glu Leu Phe Thr Arg Phe Leu Asn Ala Lys Cys Thr Thr
145                 150                 155                 160

Gln Pro Gly Thr Phe Ala Val Thr Thr Val Phe Ala Asn Ser Tyr Ser
                165                 170                 175

Leu Gly Leu Ser Pro Leu Ala Gly Ala Val Ala Ala Ile Gly Ser Val
            180                 185                 190

Gly Val Met Ala Ala Asp Asn Asp Val Thr Thr Ala Gln Gly Arg Ile
        195                 200                 205

Thr Tyr Ile Ser Pro Asp Phe Ala Ala Pro Xaa Leu Ala Gly Leu Xaa
    210                 215                 220

Asp Ala Thr Lys Val Ala Arg Thr Gly Lys Gly Ser Ser Ser Gly Gly
225                 230                 235                 240

Gly Ala Glu Gly Lys Ser Pro Ala Ala Ala Asn Xaa Ser Ala Ala Ile
                245                 250                 255

Ser Val Val Pro
            260

<210> SEQ ID NO 7
<211> LENGTH: 50
<212> TYPE: PRT
<213> ORGANISM: Homo sapiens

<400> SEQUENCE: 7

Asp Ile Asn Gly Gly Gly Ala Thr Leu Pro Gln Lys Leu Tyr Leu Thr
1               5                   10                  15

Pro Asp Val Leu Thr Ala Gly Phe Ala Pro Tyr Ile Gly Val Gly Ser
            20                  25                  30

Gly Lys Gly Lys Ile Ala Phe Leu Glu Asn Lys Tyr Asn Gln Phe Gly
        35                  40                  45

Thr Asp
    50

<210> SEQ ID NO 8
<211> LENGTH: 260
<212> TYPE: PRT
<213> ORGANISM: Homo sapiens

<400> SEQUENCE: 8

Asp Ile Asn Gly Gly Gly Ala Thr Leu Pro Gln Lys Leu Tyr Leu Thr
1               5                   10                  15

Pro Asp Val Leu Thr Ala Gly Phe Ala Pro Tyr Ile Gly Val Gly Ser
            20                  25                  30

Gly Lys Gly Lys Ile Ala Phe Leu Glu Asn Lys Tyr Asn Gln Phe Gly
        35                  40                  45

Thr Asp Thr Thr Lys Asn Val His Trp Ala Gly Ser Asp Ser Lys Leu
    50                  55                  60

Thr Ala Thr Glu Leu Ala Thr Tyr Ala Ala Asp Lys Glu Pro Gly Trp
65                  70                  75                  80

Gly Lys Leu Ile Gln Val Pro Ser Val Ala Thr Ser Val Ala Ile Pro
                85                  90                  95
```

```
Phe Arg Lys Ala Gly Ala Asn Ala Val Asp Leu Ser Val Lys Glu Leu
            100                 105                 110

Cys Gly Val Phe Ser Gly Arg Ile Ala Asp Trp Ser Gly Ile Thr Gly
            115                 120                 125

Ala Gly Arg Ser Gly Pro Ile Gln Val Val Tyr Arg Ala Glu Ser Ser
        130                 135                 140

Gly Thr Thr Glu Leu Phe Thr Arg Phe Leu Asn Ala Lys Cys Thr Thr
145                 150                 155                 160

Gln Pro Gly Thr Phe Ala Val Thr Thr Val Phe Ala Asn Ser Tyr Ser
                165                 170                 175

Leu Gly Leu Ser Pro Leu Ala Gly Ala Val Ala Ala Ile Gly Ser Val
            180                 185                 190

Gly Val Met Ala Ala Asp Asn Asp Val Thr Thr Ala Gln Gly Arg Ile
            195                 200                 205

Thr Tyr Ile Ser Pro Asp Phe Ala Ala Pro Thr Leu Ala Gly Leu Asp
        210                 215                 220

Asp Ala Thr Lys Val Ala Arg Thr Gly Lys Gly Ser Ser Ser Gly Gly
225                 230                 235                 240

Gly Ala Glu Gly Lys Ser Pro Ala Ala Asn Val Ser Ala Ala Ile
                245                 250                 255

Ser Val Val Pro
            260

<210> SEQ ID NO 9
<211> LENGTH: 50
<212> TYPE: PRT
<213> ORGANISM: Homo sapiens

<400> SEQUENCE: 9

Ser Ile Asp Gly Gly Ala Thr Leu Pro Glu Lys Leu Tyr Leu Thr
1               5                   10                  15

Pro Asp Val Leu Thr Ala Gly Phe Ala Pro Tyr Ile Gly Thr Gly Ser
            20                  25                  30

Gly Lys Gly Lys Ile Ala Phe Leu Glu Asn Ser Tyr Asn Gln Phe Gly
        35                  40                  45

Thr Asn
    50

<210> SEQ ID NO 10
<211> LENGTH: 260
<212> TYPE: PRT
<213> ORGANISM: Homo sapiens

<400> SEQUENCE: 10

Ser Ile Asp Gly Gly Ala Thr Leu Pro Glu Lys Leu Tyr Leu Thr
1               5                   10                  15

Pro Asp Val Leu Thr Ala Gly Phe Ala Pro Tyr Ile Gly Thr Gly Ser
            20                  25                  30

Gly Lys Gly Lys Ile Ala Phe Leu Glu Asn Ser Tyr Asn Gln Phe Gly
        35                  40                  45

Thr Asn Thr Thr Lys Asp Val His Trp Ala Gly Ser Asp Ser Lys Leu
    50                  55                  60

Thr Ala Ser Gln Leu Ala Thr Tyr Ala Ala Asn Lys Gln Pro Gly Trp
65                  70                  75                  80

Gly Lys Leu Ile Glu Val Pro Ser Val Ala Thr Ser Val Ala Ile Pro
                85                  90                  95
```

-continued

```
Phe Arg Lys Ala Gly Gly Asn Ala Val Asp Leu Ser Val Lys Glu Leu
            100                 105                 110
Cys Gly Val Phe Ser Gly Arg Ile Ala Asn Trp Ser Gly Ile Thr Gly
            115                 120                 125
Ala Gly Arg Ser Gly Pro Ile Gln Val Val Tyr Arg Ala Glu Val Ser
    130                 135                 140
Gly Thr Thr Glu Leu Phe Thr Arg Phe Leu Asn Ala Lys Cys Thr Thr
145                 150                 155                 160
Gln Pro Gly Thr Phe Ala Val Thr Thr Val Phe Ala Asn Ser Tyr Ser
                165                 170                 175
Leu Gly Leu Ser Pro Leu Ala Gly Ala Val Ala Ala Ile Gly Ser Val
            180                 185                 190
Gly Val Met Ala Ala Asp Asn Asp Val Thr Thr Ala Gln Gly Arg Ile
            195                 200                 205
Thr Tyr Ile Ser Pro Asp Phe Ala Ala Pro Ser Leu Ala Gly Leu Asn
        210                 215                 220
Asp Ala Thr Lys Val Ala Arg Thr Gly Lys Gly Ser Ser Ser Gly Gly
225                 230                 235                 240
Gly Ala Glu Gly Lys Ser Pro Ala Ala Ala Asn Ser Ser Ala Ala Ile
                245                 250                 255
Ser Val Val Pro
            260
```

ANTIVIRAL AGENT

The present invention describes a novel antiviral agent, in particular directed against the human immunodeficiency virus HIV.

AIDS (Acquired Immune Deficiency Syndrome) corresponds to one of the greatest human pandemics. AIDS is not actually a disease, but a set of diseases linked to opportunistic infections. These opportunistic infections can develop in the organism due to a reduction in the immune defenses of sick individuals.

AIDS is caused by infection with a retrovirus of the lentivirus family: the Human Immune Deficiency Virus (HIV), isolated in the 1980s [Barre-Sinoussi F, et al., 1983, *Science*, May 20; 220(4599):868-71; de Clavel et al., *Science*, 1986 Jul. 18; 233(4761):343-6].

There are two types of HIV viruses: HIV 1 and HIV 2 viruses.

HIV weakens the immune system by infecting the CD4 antigen-presenting cells: the CD4+ T lymphocytes, macrophages, dendritic cells and cerebral microglial cells. The infection of the CD4+ T cells, which "coordinate" the acquired immune response, is crucial in the development of the disease.

HIV infection develops in several phases which can succeed each other over time:
1. primary infection with (50 to 75% of cases) or without symptoms; this is the seroconversion phase which follows contamination.
2. a latency phase, sometimes accompanied by a state of generalized lymphadenopathy,
3. a phase with minor symptoms of human immunodeficiency virus infection,
4. the phase of profound immunodepression or generally symptomatic stage of AIDS.

During the different phases, the CD4 T cell count does not stop reducing due to the destruction of the CD4 T cells, infected or not infected.

The death of the infected cells results from the diversion of the cellular machinery of the lymphocytes, which can no longer produce their own proteins, as well as from the destruction of the membrane integrity when the newly formed viruses leave.

Moreover, infected cells expose at their membrane surface viral proteins (Env complex), proteins recognized by healthy immune cells which attach to the infected lymphocyte. This interaction results in an apoptotic process inducing the death of the healthy cells.

To date there is no treatment for curing HIV infection. In fact, an HIV-infected seropositive individual remains seropositive for life.

However, there are numerous treatments capable of blocking the development of the virus in the organism and maintaining a balance between the presence of the virus and its multiplication, and maintaining a functional immune system.

The treatments offered to HIV-seropositive patients aim to inhibit the major stages in the life cycle of the virus.

HIV infection comprises the following stages:
fusion between the host cell and the virus, and penetration,
reverse transcription of the viral RNA into DNA, by means of reverse transcriptase
integration of the viral genome into the genome of the host cell, by means of integrase
transcription of the viral genes, using the cellular machinery and the transactivator protein Tat.
synthesis of the viral proteins and their maturation, by means of viral protease
formation of the neo-viruses.

Antiretrovirals make up the therapeutic arsenal against HIV, which is being built up progressively. Some twenty antiretroviral medicaments are available on the market and their purpose is to interfere with different mechanisms, either by inhibiting the HIV enzymes necessary for its replication, or by blocking the mechanisms of entry into the target cell.

The antivirals commonly used in the treatment of HIV infection target reverse transcriptase or viral protease.

Reverse transcriptase can be inhibited by different classes of molecules: Nucleoside Reverse Transcriptase Inhibitors (NRTIs), Non-Nucleoside Reverse Transcriptase Inhibitors (NNRTIs) and Nucleoside Analog Reverse-Transcriptase Inhibitors (NARTIs).

The NRTIs were the first antivirals used to treat HIV, starting in 1985. They include in particular zidovudine (AZT), didanosine (ddI), zalcitabine (ddC), stavudine (d4T), lamivudine (3TC), abacavir (ABC) and emtricitabine (FTC). A modified NRTI also exists, the NARTI corresponding to tenofovir.

The mutations of the genome of the virus generated by the low fidelity of reverse transcription of the reverse transcriptase confer a resistance to the NRTIs upon the HIV. Cross-resistance is possible between several NRTIs.

The NNRTIs are powerful and very selective inhibitors of HIV reverse transcriptase, but target only HIV-1. Nevirapine, delavirdine and efavirenz are the three most-used NNRTIs. Protease can be inhibited by several powerful molecules which are effective on both types of virus, and the effect of which is to lead to the formation of viruses incapable of infecting other target cells. Among these molecules, there may be mentioned Atazanavir, Fosamprenavir, Lopinavir, Darunavir, Nelfinavir, Ritonavir, Saquinavir or also Tipranavir.

Other antivirals aimed at inhibiting the entry of the virus (entry inhibitor), the integration of the viral genome into the host cell (integrase inhibitor) or also inhibitors of maturation of the viral proteins (maturation inhibitors) have been marketed.

Tritherapies or multi-therapies, combining nucleoside (NRTIs), non-nucleoside (NNRTIs) inhibitors and/or antiproteases (IP), allow a reduction in the viral load below the detectability thresholds in a large number of HIV-seropositive patients. This efficacy has made possible a very marked reduction in mortality linked to HIV infection. Unfortunately, genotypes indicating resistance to an antiviral have been found in 80% of the patients and, more disturbingly, 45.5% of the viral populations are resistant to an NRTI/IP combination and 26% to a combination of three anti-HIV classes (Tamalet et al., AIDS. 2003 Nov. 7; 17(16):2383-8). This finding is of particular concern in view of the side effects linked to long-term administration of the tritherapies (lipoatrophies, lipodystrophies, hypertriglycidaemia, hypercholesterolaemia, neuropathies etc.), observed in 70% of the patients under treatment, leading to poor observance and uncontrolled discontinuation, often the cause of the appearance of resistances.

The development of less restrictive treatments, leading to fewer side effects and exhibiting no cross-resistance profile therefore remains a priority, in spite of the large number of medicaments currently on the market. For this purpose, it is essential to target other stages in the HIV replication cycle.

The HPBP protein (human phosphate binding protein) is a plasma protein which was discovered by chance during structural studies of human paraoxonase [Morales, R., et al. (2006) *Structure* 14: 601-9].

The amino acid sequence links HPBP to a family of proteins known as DING proteins, due to their very conserved N-terminal end [Diemer, H et al. (2008) *Proteins* 71: 1708-20]. The DING proteins, although ubiquitous in the eukaryotes, are surprisingly absent from the nucleotide databases [Berna, A F. Et al. (2008) *Int J Biochem Cell Biol* 40: 170-5].

Physiologically associated with human paraoxonase, a protein clearly involved in the atherosclerosis process [Shih, D M et al. (1998) *Nature* 394: 284-7], and capable of binding inorganic phosphate, HPBP is involved in atherosclerosis and used as a risk marker for cardiovascular disease (WO 2005/042572).

The structure of the HPBP has been clarified [Morales, R., et al. (2006) *Structure* 14: 601-9], and it has been shown that this protein is capable of binding inorganic phosphate (iP).

The HPBP and paraoxonase PON-1 are closely associated, and this mutual association leads to their reciprocal stabilization [Rochu D et al. *Toxicology*. 2007 Apr. 20; 233(1-3):47-59, Rochu D. et al. *Biochim Biophys Acta*. 2007 July; 1774(7):874-83, Rochu et al. *Biochem Soc Trans*. 2007 December; 35(Pt 6):1616-20].

To date, the nucleotide sequence of the human HPBP protein has not been isolated.

One of the purposes of the invention is to provide a novel treatment for combating viral infections and inflammatory diseases.

Another purpose of the invention is to provide novel antiviral pharmaceutical compositions which exhibit reduced side effects, and are better tolerated by patients.

One of the purposes of the invention is also to provide novel antiviral compositions acting on other targets of the viral cycle.

The present invention describes the use of a composition comprising or constituted by at least one element chosen from:
 a specific protein comprising the amino acid sequence SEQ ID NO: 5,
 a protein homologous to said specific protein, possessing an amino acid sequence exhibiting at least 72% homology with the sequence SEQ ID NO: 5,
provided that said previous proteins interact with the transcription factor C/EBPβ and/or the viral protein Tat,
for the preparation of a medicament intended for the prevention or treatment of pathologies associated with a viral infection or an inflammation.

The present invention relates to the use of a composition comprising or constituted by at least one element chosen from:
 a specific protein comprising or constituted by the amino acid sequence SEQ ID NO: 5, and
 a protein homologous to said specific protein, possessing an amino acid sequence exhibiting at least 72% homology with the sequence SEQ ID NO: 5,
provided that said previous proteins interact with the transcription factor C/EBPβ and/or the viral protein Tat,
for
 the preparation of a medicament intended for the prevention or treatment of pathologies associated with a viral infection or an inflammation, provided that, within the context of pathologies linked to inflammation, said element is not any one of the proteins SEQ ID NO: 1 to 3, or
 the implementation of a method, in particular in vitro, for measuring susceptibility to a viral infection.

In an advantageous embodiment, the invention relates to the use of a composition comprising or constituted by at least one element chosen from:
 a specific protein comprising or constituted by the amino acid sequence SEQ ID NO: 5, and
 a protein homologous to said specific protein, possessing an amino acid sequence exhibiting at least 72% homology with the sequence SEQ ID NO: 5,
provided that said previous proteins interact with the transcription factor C/EBPβ and/or the viral protein Tat,
for the preparation of a medicament intended for the prevention or treatment of pathologies associated with a viral infection.

An advantageous embodiment of the invention describes the use of a composition as defined previously, where said specific protein is constituted by an amino acid sequence chosen from the following amino acid sequences: SEQ ID NO: 5, SEQ ID NO: 7 and SEQ ID NO: 9.

An advantageous embodiment of the invention describes the use of a composition as defined previously, comprising or constituted by at least one element chosen from:
 a specific protein comprising or constituted by the amino acid sequence SEQ ID NO: 6, and
 a protein homologous to said specific protein, possessing an amino acid sequence exhibiting at least 72% homology with the sequence SEQ ID NO: 6,
provided that said previous proteins interact with the transcription factor C/EBPβ and/or the viral protein Tat.

An advantageous embodiment of the invention describes the use of a composition as defined previously, where said specific protein is constituted by an amino acid sequence chosen from the following amino acid sequences: SEQ ID NO: 6, SEQ ID NO: 8 and SEQ ID NO: 10.

An advantageous embodiment of the invention describes the use of a composition as defined previously, comprising or constituted by at least one element chosen from:
 a specific protein comprising or constituted by the amino acid sequence SEQ ID NO: 1, and
 a protein homologous to said specific protein, possessing an amino acid sequence exhibiting at least 72% homology with the sequence SEQ ID NO: 1
provided that said previous proteins interact with the transcription factor C/EBPβ and/or the viral protein Tat.

An advantageous embodiment of the invention describes the use of a composition as defined previously, where said specific protein is constituted by an amino acid sequence chosen from the following amino acid sequences: SEQ ID NO: 1, SEQ ID NO: 2 and SEQ ID NO: 3.

An advantageous embodiment of the invention describes the use of a composition as defined previously, where said specific protein is constituted by an amino acid sequence chosen from the following amino acid sequences: SEQ ID NO: 1, SEQ ID NO: 2 and SEQ ID NO: 3, for the preparation of a medicament within the context of the treatment of diseases associated with a viral infection.

The present invention is based on the unexpected demonstration by the Inventors of antiviral and anti-inflammatory properties of the HPBP protein, and more particularly of a protein comprising the sequence SEQ ID NO: 5.

The sequence SEQ ID NO: 5 corresponds to the 50 first amino acids of the sequence SEQ ID NO: 1 defined below.

The sequence SEQ ID NO: 6 corresponds to the 260 first amino acids of the sequence SEQ ID NO: 1 defined below.

More precisely, the invention is based on the demonstration made by the Inventors of the inhibiting action of the HPBP protein, or of its fragments, on the transcription, in particular of viral genes or of genes involved in inflammation, requiring the transcription factor C/EBPβ.

In the invention, by "specific protein", is meant any protein, peptide, fragment of proteins or peptides or known, the synthesis of which takes place within a living organism, generally without external human intervention, and isolated from its natural context.

The HPBP protein can be defined by its amino acid sequence SEQ ID NO: 1. The three-dimensional structure of the HPBP is shown in FIG. 1.

In the invention "a protein homologous to said specific protein", corresponds to a protein derived from said specific protein, said derived protein being obtained by mutation, suppression or addition of one or more amino acids to the sequence of said specific protein.

More particularly, "a protein homologous to said specific protein" is defined in the invention as a protein obtained by substitution of one or more amino acids provided that said homologous protein exhibits at least 72% homology with the sequence SEQ ID NO: 5, and that it has the following sequence: D-I-N-G-G-G-Xn-F-G, where X represents any one of the 20 natural amino acids, and n varies from approximately 30 to approximately 40, in particular 40.

The data on the interaction between the protein Tat and the HPBP protein are presented in the Examples part hereafter.

From these data, a person skilled in the art can find the minimum essential amino acids allowing the HPBP/Tat combination.

In the invention, by "viral infection" is meant any disease triggered by a virus and the propagation of this virus in the organism (and at the expense of the organism). The measurement of a viral infection is commonly carried out by the detection in the infected organism of specific viral markers. For example, for HIV, the marker p24 is evidence of infection. HIV can also be detected by measuring the viral load, i.e. the quantity of viral RNA.

By "inflammation", is meant in the invention a stereotypical immune defense reaction of the organism involving, among other things, vasodilation. Among other mechanisms, inflammation is characterized by the secretion of pro-inflammatory factors such as IL-6, TNF-α or the chemokine MCP-1. Inflammation can be measured by assay of the abovementioned pro-inflammatory factors.

In the invention, "the pathologies associated with inflammation" can be represented by rheumatoid arthritis, autoimmune diseases and in particular lupus, more particularly disseminated erythematous lupus, food allergies or allergies of the respiratory tract, in particular pollen allergies, Sjögren's syndrome, scleroderma (systemic sclerosis), dermatomyositis, polymyositis, polymyalgia rheumatica, osteoarthritis, septic arthritis or also vascularity.

St. John's wort protein $p27^{SJ}$, represented by the amino acid sequence SEQ ID NO: 4, is excluded from the invention as it exhibits 71% sequence homology with the sequence SEQ ID NO: 1.

The terms "interacts with the transcription factor C/EBPβ and/or the viral protein Tat" mean that there can be an interaction with the C/EBPβ protein alone or with the protein Tat alone, or also that there is an interaction with the C/EBPβ protein and with the Tat protein. The abovementioned terms can therefore be interpreted as follows: "interacts with the transcription factor C/EBPβ, or interacts with the viral protein Tat or also interacts with the transcription factor C/EBPβ and the viral protein Tat".

By "interacts with the transcription factor C/EBPβ" is meant within the invention that there is a direct, chemical, electrostatic or ionic bond between a protein, homologue or variant of the HPBP protein, and the transcription factor C/EBPβ. This interaction can be revealed by standard methods known to a person skilled in the art, such as co-immunoprecipitation, or also an ELISA test as defined hereafter, said techniques not being limitative.

By "interacts with the Tat protein" is meant within the invention that there is a direct, chemical, electrostatic or ionic bond between a protein, homologue or variant of the HPBP protein, and the Tat protein. This interaction can be revealed by standard methods known to a person skilled in the art, such as co-immunoprecipitation, or also an ELISA test as defined hereafter, said techniques not being limitative The C/EBP family (CCAAT-enhancer-binding proteins) is constituted by a large number of "leucine-zipper" type transcription factors. These factors are proteins capable of binding to DNA motifs rich in CCAAT motifs, said CCAAT motifs being present in the sequence of the promoters of numerous genes, and of regulating the expression of the genes. These factors are known to play an important role in specialized functions of the hepatocytes, adipocytes and macrophages [Li H, et al. *Cell Mol Immunol;* 2007 December; 4(6):407-18].

CCAAT-type motifs have been described either in viral gene promoters, or in the long terminal repeat (LTR) sequences of the retroviruses. The presence of the CCAAT sites and the binding of the factor C/EBPβ in particular has the consequence of inducing the expression of the genes under the control of these regulatory sequences. There can be mentioned as examples of viruses, without however being limitative, the HIV virus, the hepatitis virus, in particular hepatitis B, the human papillomaviruses, the adenoviruses including adenovirus Ad-36 and the herpes virus. [Kinoshita S M, et al. *Proc Natl Acad Sci USA;* 2008 Sep. 30; 105(39):15022-7; Wooldridge T R, et al. *Virology Volume* 374, Issue 2, 10 May 2008, Pages 371-380; Ralph W M Jr et al.; *J Gen Virol.* 2006 January; 87(Pt 1):51-9; Rogers P M, et al.; *Int J Obes* (Lond). 2008 March; 32(3):397-406].

C/EBPβ, also called NF-IL6 (Nuclear Factor IL-6) plays an important role in the regulation of the genes involved in the immune and inflammatory response, and in particular interacts with the IL-1 response element of the promoter of the pro-inflammatory IL-6 gene. C/EBPβ has also been shown to be capable of inducing the expression of the TNFα genes or of the monocyte chemoattractant factor MCP-1.

The sequence SEQ ID NO: 2 corresponds to the amino acid sequence of the human HPBP protein, having phosphate binding properties, which has been isolated from human plasma. The protocol for purification of the HPBP having a defined amino acid sequence consisting of the sequence SEQ ID NO: 2 is detailed in the international application WO 2005/042572. This method of purification is based on its co-purification with human paraoxonase PON-1. The purification of HPBP from the HPBP/PON-1 complex is carried out according to the protocol described in Renault et al. [Renault et al. *J Chromatogr B Analyt Technol Biomed Life Sci.* 2006 May 19; 836(1-2):15-21]. The detailed protocol is described in the Examples section hereafter.

The sequence SEQ ID NO: 3 corresponds to the amino acid sequence of a protein exhibiting approximately 90% identity with the human HPBP protein, and having phosphate binding properties, i.e. inorganic phosphate binding properties.

The sequence SEQ ID NO: 7 corresponds to the first 50 amino acids of the sequence SEQ ID NO: 2.

The sequence SEQ ID NO: 8 corresponds to the first 260 amino acids of the sequence SEQ ID NO: 2.

The sequence SEQ ID NO: 9 corresponds to the first 50 amino acids of the sequence SEQ ID NO: 3.

The sequence SEQ ID NO: 10 corresponds to the first 260 amino acids of the sequence SEQ ID NO: 3.

The phosphate binding properties are measured by the following radioactive phosphate labelling test:

The protein is bound to a nitrocellulose membrane (for example dot blot aspiration). The membrane is then incubated with a 50 mM Tris buffer, pH 8.0, containing radioactive phosphate ($^{32}$P, 10 mCi/mL, Amersham-Biosciences) 2M. The membrane is then washed twice with the buffer no longer comprising radioactive phosphate, and the membrane thus washed is brought into contact with an autoradiographic film for approximately 45 min. The film is then developed and the prints from the film make it possible to determine the HPBP's phosphate binding capacity.

According to another embodiment, in the use described above, said pathologies are caused by viruses, the gene transcription of which requires the transcription factor C/EBPβ, and in particular HIV viruses, hepatitis viruses or herpes viruses.

The transcription of the viral genes is necessary for their multiplication. The genome of viruses contains genes essential for the synthesis of the proteins specific to the virus (envelope proteins, enzymes etc.), and in particular proteins having powerful transactivating properties such as Tat for HIV, ICP27 for the HSV virus, or the HBV X protein.

In the invention, by "hepatitis viruses" is meant the viruses inducing any acute or chronic inflammation of the liver. The prior art describes 7 viruses responsible for hepatitis: the HAV, HBV, HCV, HDV, HEV, HFV and HDV viruses.

Another advantageous embodiment of the invention describes the use of a composition as defined previously, in which said HIV viruses are the HIV-1 or HIV-2 viruses.

In the invention the HIV-1 viruses are represented by their M, O or N groups, and also the sub-groups or classes of the M group: A, B, C, D, F, G, H, J and K.

The mutant viral strains, due to the low fidelity of the reverse transcriptase, as well as the mixed strains (originating from a cell infected with two distinct viral strains) are covered by the invention.

The mutant viral strains can also lead to resistance to commonly-used treatments; these are so-called resistant strains.

An advantageous embodiment of the invention describes the use as defined above, in which said composition is administered at a dose from approximately 0.1 nM to approximately 1 mM, advantageously from approximately 10 nM to approximately 100 nM, in particular from approximately 30 nM to approximately 70 nM, preferentially approximately 50 nM.

The HPBP protein has a mass of 38,000 Da (38 kDa). Thus, for an adult having on average a blood volume of 5 L, the composition according to the invention can be administered at a dose from approximately 0.3 μg/kg to approximately 1 mg/kg, in particular from approximately 30 μg/kg to approximately 300 μg/kg, preferentially from approximately 90 μg/kg to approximately 210 μg/kg, more preferentially approximately 150 μg/kg.

The composition of the invention can be administered in particular by intravenous route, by sub-cutaneous route, by systemic route, by local route by means of infiltrations or orally. The treatment can be continuous or sequential, i.e. by means of a perfusion delivering said composition in a continuous and optionally constant manner, or in a discontinuous form, by one or more daily oral administrations or injections, optionally repeated for several days, either consecutive days, or with a period without treatment between the administrations.

Advantageously, the invention describes the use of a composition as defined previously, in combination with at least one compound possessing antiviral properties and/or with at least one compound possessing anti-inflammatory properties.

By "compound possessing antiviral properties" is meant within the invention any protein compound, or compound originating from chemical synthesis, which is capable of partially or completely inhibiting at least one of the events necessary to the life cycle of the viruses.

By life cycle of viruses is meant within the invention all the stages in the life of a virus, from infection of the host cell to the production of new viruses.

As a non-limitative example, a compound possessing antiviral properties according to the invention can inhibit within the context of HIV: the processes of cell fusion and entry of the virus, the reverse transcription processes, the processes of integration of the virus genome into the host cell genome, the processes of transcription of the viral genes, the processes of virion formation or also the processes of maturation of the different constituents of the newly-formed virions.

By "compound possessing anti-inflammatory properties" is meant within the invention any natural compound, or compound originating from chemical synthesis, which is capable of partially or completely inhibiting at least one of the events necessary to establish an inflammatory response as defined previously.

Another preferred embodiment of the invention describes the use previously mentioned, in which said antiviral compound possessing antiviral properties is chosen from the antiprotease inhibitors, in particular ritonavir, indinavir, saquinavir and nelfinavir, reverse transcriptase inhibitors, in particular AZT, ddI, ddC, 3TC, d4T, nevirapine, delavirdine and efavirenz, fusion inhibitors, entry inhibitors and integrase inhibitors.

The composition according to the invention can also be used in combination with the antiviral compositions listed in Table 1 below:

TABLE 1

Trade names of the different antivirals used for HIV treatment, as well as their specificity of action.

| | |
|---|---|
| Intelence ® (TMC 125/etravirine) Tibotec - | Non-nucleoside reverse transcriptase inhibitor |
| Agenerase ®(APV/amprenavir) GSK - | Protease inhibitor |
| Aptivus ®(TPV/tipranavir) Boehringer - | Protease inhibitor |
| Crixivan ®(IDV/indinavir) MSD - | Protease inhibitor |
| Invirase ®(SQV/saquinavir) Roche - | Protease inhibitor |
| Kaletra ®(LPV,r/lopinavir + ritonavir) Abbott | Protease inhibitor |
| Norvir ®(ritonavir) Abbott - | Protease inhibitor |
| Prezista ®(TMC 114/darunavir) Tibotec/Janssen-Cilag - | Protease inhibitor |
| Reyataz ®(ATZ/atazanavir) BMS - | Protease inhibitor |
| Telzir ®(APV/fosamprenavir) GSK - | Protease inhibitor |
| Viracept ®(nelfinavir) Roche - | Protease inhibitor |
| Fuzeon ®(T20/enfuvirtide) Roche - | Fusion inhibitor |
| Celsentri ®(maraviroc) Pfizer - | Entry inhibitor |
| Isentress ®(MK 0518/raltegravir) Merck - | Integrase inhibitor |
| Rescriptor ®(delavirdine) Agouron - | Non-nucleoside reverse transcriptase inhibitor |

TABLE 1-continued

Trade names of the different antivirals used for HIV treatment, as well as their specificity of action.

| | |
|---|---|
| Sustiva ®(EFV/efavirenz) BMS - | Non-nucleoside reverse transcriptase inhibitor |
| Viramune ®(nevirapine) Boehringer - | Non-nucleoside reverse transcriptase inhibitor |
| Combivir ®(Retrovir ® + Epivir ®) GSK - | Nucleoside reverse transcriptase inhibitor |
| Emtriva ®(FTC, emtricitabine) Gilead - | Nucleoside reverse transcriptase inhibitor |
| Epivir ®(3TC, lamivudine) GSK - | Nucleoside reverse transcriptase inhibitor |
| Kivexa ®(Ziagen ® + Epivir ®) GSK - | Nucleoside reverse transcriptase inhibitor |
| Retrovir ®(AZT/zidovudine) QSK - | Nucleoside reverse transcriptase inhibitor |
| Trizivir ®(Retrovir ® + Epivir ® + Ziagen ®) GSK - | Nucleoside reverse transcriptase inhibitor |
| Videx ®(ddI/didanosine) BMS - | Nucleoside reverse transcriptase inhibitor |
| Viread ®(TDF/tenofovir) Gilead - | Nucleoside reverse transcriptase inhibitor |
| Zerit ®(d4T/stavudine) BMS - | Nucleoside reverse transcriptase inhibitor |
| Ziagen ®(ABC/abacavir) GSK - | Nucleoside reverse transcriptase inhibitor |
| Truvada ®(Emtriva ® + Viread ®) Gilead - | Nucleoside reverse transcriptase inhibitor |
| Atripla ®(Sustiva ® + Emtriva ® + Viread ®) BMS/GILEAD | Nucleoside and non-nucleoside reverse transcriptase inhibitor |

Another preferred embodiment of the invention describes the previously-mentioned use in which said compound possessing anti-inflammatory properties is chosen from the synthetic glucocorticoids: short-acting (prednisone), intermediate-acting (paramethasone), long-acting (betamethasone), or non-steroid anti-inflammatories such as the salicylates (acetylsalicylic acid, methyl salicylate or diflunisal), the arylalkanoic acids (indometacin, sulindac, or diclofenac), 2-arylpropionic acids (profenes) (ibuprofen, ketoprofen, naproxen, or ketorolac), N-arylanthranilic acids (fenamic acids) (mefenamic acid), oxicams (piroxicam or meloxicam), coxibs (celecoxib, rofecoxib, valdecoxib, parecoxib or etoricoxib) or also sulphonanilides (nimesulide).

Another advantageous embodiment of the invention also describes the use of a composition as defined previously, for the preparation of a medicament intended for the prevention or treatment of pathologies associated with a viral infection or an inflammation, said composition and said antiviral compound possessing antiviral properties or said antiviral compound possessing anti-inflammatory properties being used simultaneously, separately or spread over time.

In the invention, the previous composition is in combination with an antiviral compound possessing antiviral or anti-inflammatory properties in a ratio of approximately 10/1 to approximately 1/10, preferentially approximately 5/1 to approximately 1/5, more particularly approximately 2/1 to approximately 1/2, and in particular 1/1.

The invention also describes a composition comprising or constituted by at least one element chosen from:
  a specific protein comprising or constituted by the amino acid sequence SEQ ID NO: 5,
  a protein homologous to said specific protein, possessing an amino acid sequence exhibiting at least 72% homology with the sequence SEQ ID NO: 5,
provided that said previous proteins interact with the transcription factor C/EBPβ and/or the viral protein Tat,
for the preparation of a medicament intended for the prevention or treatment of pathologies associated with a viral infection or an inflammation.

The invention also describes a combination product comprising at least one element as defined previously and at least one compound possessing antiviral properties and/or anti-inflammatory properties.

The invention also describes a combination product comprising at least one element as defined previously and at least one compound possessing antiviral properties.

An advantageous embodiment of the invention describes an abovementioned combination product for the prevention or treatment of pathologies associated with a viral infection or an inflammation, said composition and said antiviral compound possessing antiviral properties being in particular used simultaneously, separately or spread over time.

An advantageous embodiment of the invention describes an abovementioned combination product, for the prevention or treatment of pathologies associated with a viral infection, said composition and said antiviral compound possessing antiviral properties being in particular used simultaneously, separately or spread over time.

The invention also describes a pharmaceutical composition comprising as active ingredient at least one element chosen from
  a specific protein comprising or constituted by the amino acid sequence SEQ ID NO: 5, and
  a protein homologous to said specific protein, possessing an amino acid sequence exhibiting at least 72% homology with the sequence SEQ ID NO: 5,
provided that said previous proteins interact with the transcription factor C/EBPβ and/or the viral protein Tat,
and at least one antiviral compound possessing antiviral properties, and/or a compound possessing anti-inflammatory properties
in combination with a pharmaceutically acceptable vehicle.

The invention also describes a pharmaceutical composition comprising as active ingredient
* at least one element chosen from
  a specific protein comprising or constituted by the amino acid sequence SEQ ID NO: 5, and
  a protein homologous to said specific protein, possessing an amino acid sequence exhibiting at least 72% homology with the sequence SEQ ID NO: 5, provided that said previous proteins interact with the transcription factor C/EBPβ and/or the viral protein Tat,
and
* at least one antiviral compound possessing antiviral properties,
in combination with a pharmaceutically acceptable vehicle.

In a preferred embodiment, the invention describes a pharmaceutical composition as defined previously, where said specific protein is constituted by the amino acid sequence chosen from the following amino acid sequences: SEQ ID NO: 5, SEQ ID NO: 7 and SEQ ID NO: 9.

Another preferred embodiment of the invention describes a pharmaceutical composition as defined previously, comprising as active ingredient at least one element chosen from
  a specific protein comprising or constituted by the amino acid sequence SEQ ID NO: 6, and
  a protein homologous to said specific protein, possessing an amino acid sequence exhibiting at least 72% homology with the sequence SEQ ID NO: 6, and
provided that said previous proteins interact with the transcription factor C/EBPβ and/or the viral protein Tat,
and at least one compound possessing antiviral properties and/or anti-inflammatory properties,
in combination with a pharmaceutically acceptable vehicle.

Another preferred embodiment of the invention describes a pharmaceutical composition as defined previously, comprising as active ingredient
* at least one element chosen from
    a specific protein comprising or constituted by the amino acid sequence SEQ ID NO: 6, and
    a protein homologous to said specific protein, possessing an amino acid sequence exhibiting at least 72% homology with the sequence SEQ ID NO: 6, and
provided that said previous proteins interact with the transcription factor C/EBPβ and/or the viral protein Tat,
and
* at least one compound possessing antiviral properties,
in combination with a pharmaceutically acceptable vehicle.

In a preferred embodiment, the invention describes a pharmaceutical composition as defined previously, where said specific protein is constituted by the amino acid sequence chosen from the following amino acid sequences: SEQ ID NO: 6, SEQ ID NO: 8 and SEQ ID NO: 10.

Another preferred embodiment of the invention describes a pharmaceutical composition as defined previously, comprising as active ingredient at least one element chosen from
    a specific protein comprising or constituted by the amino acid sequence SEQ ID NO: 1, and
    a protein homologous to said specific protein, possessing an amino acid sequence exhibiting at least 72% homology with the sequence SEQ ID NO: 1, and
provided that said previous proteins interact with the transcription factor C/EBPβ and/or the viral protein Tat,
and at least one compound possessing antiviral properties and/or anti-inflammatory properties,
in combination with a pharmaceutically acceptable vehicle.

Another preferred embodiment of the invention describes a pharmaceutical composition as defined previously, comprising as active ingredient
* at least one element chosen from
    a specific protein comprising or constituted by the amino acid sequence SEQ ID NO: 1, and
    a protein homologous to said specific protein, possessing an amino acid sequence exhibiting at least 72% homology with the sequence SEQ ID NO: 1, and
provided that said previous proteins interact with the transcription factor C/EBPβ and/or the viral protein Tat,
and
* at least one compound possessing antiviral properties,
in combination with a pharmaceutically acceptable vehicle.

In a preferred embodiment, the invention describes a pharmaceutical composition as defined previously, where said specific protein is constituted by the amino acid sequence chosen from the following amino acid sequences: SEQ ID NO: 1, SEQ ID NO: 2 and SEQ ID NO: 3.

In the invention, the previous pharmaceutical composition is in combination with a compound possessing antiviral properties in a ratio of approximately 10/1 to approximately 1/10, preferentially approximately 5/1 to approximately 1/5, more particularly approximately 2/1 to approximately 1/2, and in particular 1/1.

For an adult possessing on average a blood volume of 5 L, the composition according to the invention can be administered at a dose from approximately 0.3 µg/kg to approximately 1 mg/kg, in particular from approximately 30 µg/kg to approximately 300 µg/kg, preferentially from approximately 90 µg/kg to approximately 210 µg/kg, more preferentially approximately 150 µg/kg.

In the invention, the previous pharmaceutical composition is in combination with a compound possessing anti-inflammatory properties in a ratio of approximately 10/1 to approximately 1/10, preferentially approximately 5/1 to approximately 1/5, more particularly approximately 2/1 to approximately 1/2, and in particular 1/1.

For an adult possessing on average a blood volume of 5 L, the composition according to the invention can be administered at a dose from approximately 0.3 µg/kg to approximately 1 mg/kg, in particular from approximately 30 µg/kg to approximately 300 µg/kg, preferentially from approximately 90 µg/kg to approximately 210 µg/kg, more preferentially approximately 150 µg/kg.

In the invention, the previous pharmaceutical composition is in combination with a compound possessing antiviral properties and a compound possessing anti-inflammatory properties in a ratio of approximately 10/1/1 to approximately 1/10/10, preferentially approximately 5/1/1 to approximately 1/5/5, more particularly approximately 2/1/1 to approximately 1/2/2, and in particular 1/1/1.

For an adult possessing on average a blood volume of 5 L, the composition according to the invention can be administered at a dose from approximately 0.3 µg/kg to approximately 1 mg/kg, in particular from approximately 30 µg/kg to approximately 300 µg/kg, preferentially from approximately 90 µg/kg to approximately 210 µg/kg, more preferentially approximately 150 µg/kg.

The pharmaceutical composition according to the invention can optionally be a neutracetic or cosmetic composition.

Another advantageous embodiment of the invention describes a pharmaceutical composition as defined above, in which said pathologies are caused by infection with the HIV viruses, the hepatitis viruses or the herpes viruses.

In another advantageous embodiment, the invention describes a pharmaceutical composition previously described, in which said HIV viruses are the HIV-1 or HIV-2 viruses.

Another advantageous embodiment of the invention describes a pharmaceutical composition defined previously, in which said antiviral compound is chosen from the antiprotease inhibitors, in particular ritonavir, indinavir, saquinavir and nelfinavir, and the reverse transcriptase inhibitors, in particular AZT, ddI, ddC, 3TC, d4T, nevirapine, delavirdine and efavirenz.

Another advantageous embodiment of the invention describes a pharmaceutical composition defined previously, in which said anti-inflammatory compound is chosen from the synthetic glucorticoids, in particular prednisone, prednisolone, methylprednisolone, dexamethasone, betamethasone or also paramethasone, the non-steroid anti-inflammatories, in particular the salicylates such as methyl salicylate and diflunisal, the arylalkanoic acids such as indometacin, sulindac and diclofenac, the 2-arylpropionic acids (profenes) such as ibuprofen, ketoprofen, naproxen and ketorolac, the N-arylanthranilic acids (fenamic acids) such as mefenamic acid, the oxicams such as piroxicam and meloxicam, the coxibs such as celecoxib, rofecoxib, valdecoxib, parecoxib, or etoricoxib, and the sulphonanilides such as nimesulide.

The invention also describes a method for diagnosing, in particular in vitro, resistance to infection by a virus, in a biological sample originating from an individual, comprising,
    determination of the quantity of specific protein as defined previously in said biological sample,
    comparison of said quantity obtained in the following stage with the quantity of specific protein in at least one reference sample,
    determination, from the previous comparison, of the resistance to a viral infection.

By "resistance to infection by a virus", is meant within the invention the ability that certain individuals have not to be infected by viruses. In fact, under normal conditions, a non-resistant individual, when brought into the presence of a virus for the first time (primary infection), is normally infected with said virus. In certain rare cases, certain individuals are resistant to the primary infection, i.e. when the individual is first brought into contact with the virus, the latter is not capable of infecting said individual.

In the invention, by "infect" is meant the ability that a virus possesses to turn the cellular machinery of the host cell to its advantage, i.e. to produce new viruses or virions. The fact of "not being capable of infecting" signifies that the virus is not capable of effectively achieving the production of new virions.

In the method of the invention, the quantity of HPBP protein is determined in a biological sample such as blood, plasma, lymph or also urine. "The determination of the quantity" means that the HPBP protein is assayed in said sample.

The assay methods for the HPBP protein can be immunological methods known to a person skilled in the art. For example, the Western Blot techniques (immunodetection), immunoprecipitation, or the ELISA techniques can be used; the RIA techniques can also be implemented.

An example of detection of the HPBP protein is the ELISA described in the Example part. Briefly, a monoclonal or polyclonal antibody directed against the HPBP protein is immobilized on a plate. After washings, the sample is incubated with the plate or said antibodies are immobilized. After washings, a second antibody directed against the HPBP protein is incubated with said plate previously incubated with the sample. Finally, after washing, the plate is incubated with an antibody directed against the constant part of the previous antibodies, said antibodies directed against the constant part being coupled with a molecule allowing detection such as peroxidase (HRP).

The assay of the HPBP protein thus carried out can be quantified by photometric or spectroscopic techniques well known to a person skilled in the art.

The concentration of the HPBP protein is compared with the concentration of at least one reference sample. The reference sample can correspond:
either to a sample originating from a healthy individual,
or to a sample originating from an individual having been infected with a virus, in particular an individual infected with HIV, said individual having developed, or not, symptoms linked to said viral infection, or
a sample originating from an individual resistant to the viral infection, said resistant individual having been in contact one or more times with said virus without ever being infected.

The method according to the invention makes it possible to determine whether an individual is resistant to a viral infection.

If the HPBP level is similar to, or substantially the same as that of a healthy individual or of an individual infected with a virus, the sample from the individual is considered as being capable of being infected with said virus: the individual is not resistant.

If the HPBP level is high, or similar to that of an individual resistant to a viral infection, the individual from whom the sample tested has been taken is considered as being resistant to a viral infection.

The invention also relates to a previously-defined method of diagnosis, in which said infection is due to infection with the HIV viruses, in particular the HIV-1 or HIV-2 virus, the hepatitis viruses or the herpes viruses.

The invention also describes a pharmaceutical composition comprising as active ingredient at least one element chosen from
a specific protein characterized in that it comprises or is constituted by an amino acid sequence chosen from SEQ ID NO: 5, SEQ ID NO: 6 and SEQ ID NO:1, and
a protein homologous to said specific protein, characterized in that it possesses at least 72% homology with one of the abovementioned sequences,
provided that said previous proteins interact with the transcription factor C/EBPβ and/or the viral protein Tat,
and at least one compound possessing antiviral properties and/or at least one compound possessing anti-inflammatory properties,
said antiviral compound being in particular chosen from the antiprotease inhibitors, such as ritonavir, indinavir, saquinavir and nelfinavir, and the reverse transcriptase inhibitors, such as AZT, ddI, ddC, 3TC, d4T, nevirapine, delavirdine and efavirenz,
in combination with a pharmaceutically acceptable vehicle, for the prevention or treatment of pathologies associated with a viral infection or an inflammation.

The invention also describes a pharmaceutical composition comprising as active ingredient
* at least one element chosen from
a specific protein characterized in that it comprises or is constituted by an amino acid sequence chosen from SEQ ID NO: 5, SEQ ID NO: 6 and SEQ ID NO:1, and
a protein homologous to said specific protein, characterized in that it possesses at least 72% homology with one of the abovementioned sequences,
provided that said previous proteins interact with the transcription factor C/EBPβ and/or the viral protein Tat,
and
* at least one compound possessing antiviral properties chosen in particular from the antiprotease inhibitors, such as ritonavir, indinavir, saquinavir and nelfinavir, and the reverse transcriptase inhibitors, such as AZT, ddI, ddC, 3TC, d4T, nevirapine, delavirdine and efavirenz,
in combination with a pharmaceutically acceptable vehicle, for the prevention or treatment of pathologies associated with a viral infection.

The invention also describes in an advantageous embodiment a pharmaceutical composition as defined previously where said specific protein comprises or is constituted by the amino acid sequence chosen from the following amino acid sequences: SEQ ID NO: 1, SEQ ID NO: 2, SEQ ID NO: 3, SEQ ID NO: 6, SEQ ID NO: 7, SEQ ID NO: 8, SEQ ID NO: 9 or SEQ ID NO: 10.

The present invention is better illustrated by the following examples and figures, the latter not being limitative in character.

FIG. 1 shows the three-dimensional structure of the HPBP protein.

FIG. 2 shows an electrophoresis gel stained with silver nitrate showing in track A the purification of the PON-1/HPBP complex, and in tracks B and C the products of the separation after passing the PON-1 and HPBP proteins respectively through a hydroxylapatite column. The molecular weights are indicated.

Figure 3:
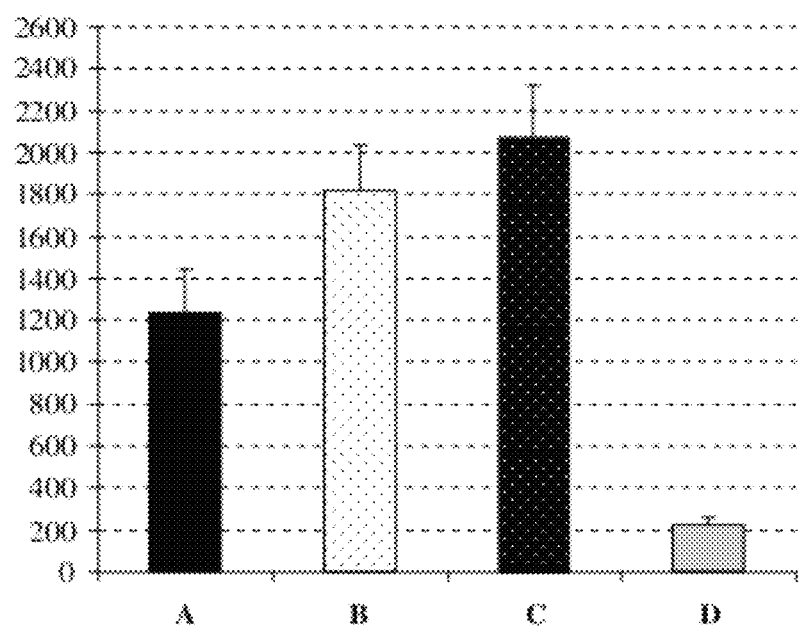

FIG. 3 represents the measurement of the transcriptional activity of the HIV virus in Jurkat lines. The values represent the luciferase activity. Track A represents the untreated cells, track B represents the cells treated with the mixture of PON-1 and HPBP proteins, track C represents the cells treated with the PON-1 protein, track D represents the cells treated with the HPBP protein.

Figure 4:
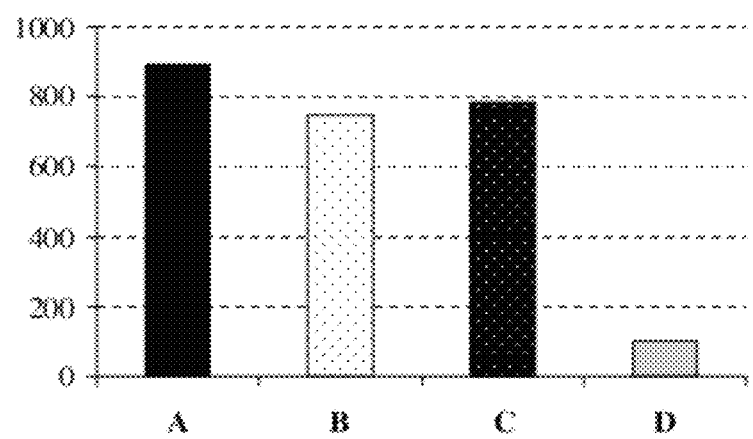

FIG. 4 represents the measurement of the replication activity of the HIV virus in Jurkat lines. The values represent the quantity of p24 protein. Track A represents the untreated cells, track B represents the cells treated with the mixture of PON-1 and HPBP proteins, track C represents the cells treated with the PON-1 protein, track D represents the cells treated with the HPBP protein.

Figure 5:
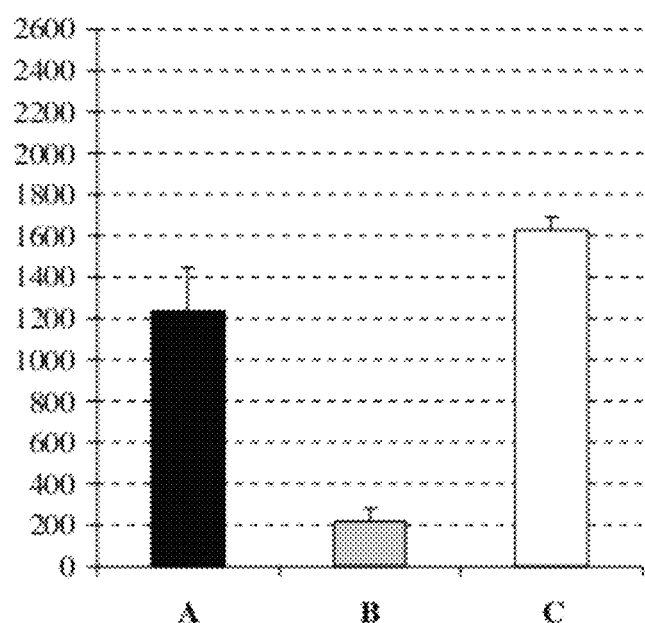

FIG. 5 represents the measurement of the transcriptional activity of the HIV virus in Jurkat lines. The values represent the luciferase activity. Track A represents the untreated cells, track B represents the cells treated with the HPBP protein, track C represents the cells treated with AZT.

Figure 6:
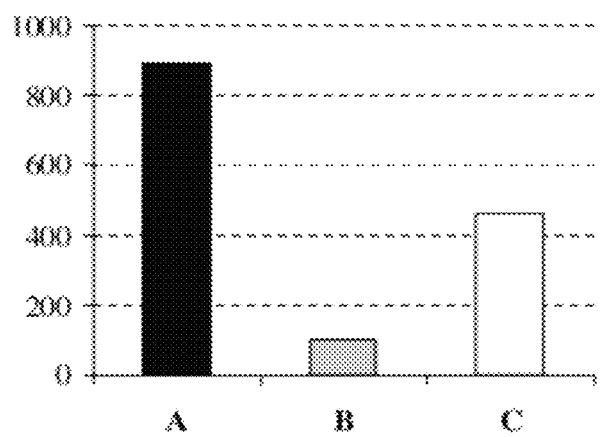

FIG. 6 represents the measurement of the replication activity of the HIV virus in Jurkat lines. The values represent the quantity of p24 protein. Track A represents the untreated cells, track B represents the cells treated with the HPBP protein, track C represents the cells treated with AZT.

Figure 7:
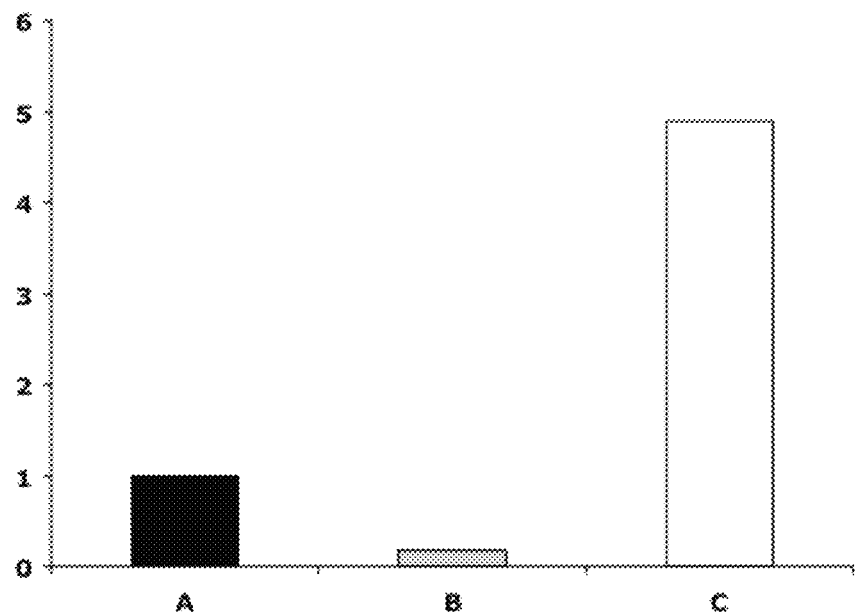

FIG. 7 shows the measurement of the transcriptional activity of the HIV virus in Jurkat lines. The values represent the level of induction of the transcription. Track A represents the untreated cells, track B represents the cells treated with HPBP, track C represents the cells treated with potato DING protein.

Figure 8:
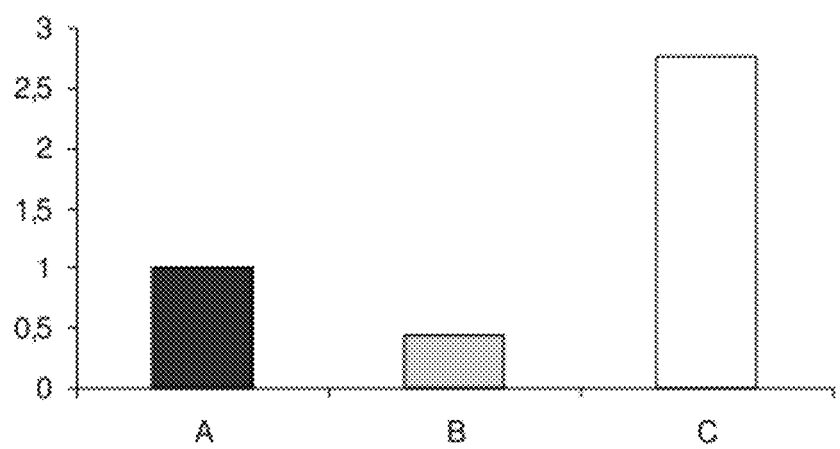

FIG. 8 shows the measurement of the replication activity of the HIV virus in Jurkat lines. The values represent the level of induction of the replication. Track A represents the untreated cells, track B represents the cells treated with HPBP, track C represents the cells treated with potato DING protein.

Figure 9A:
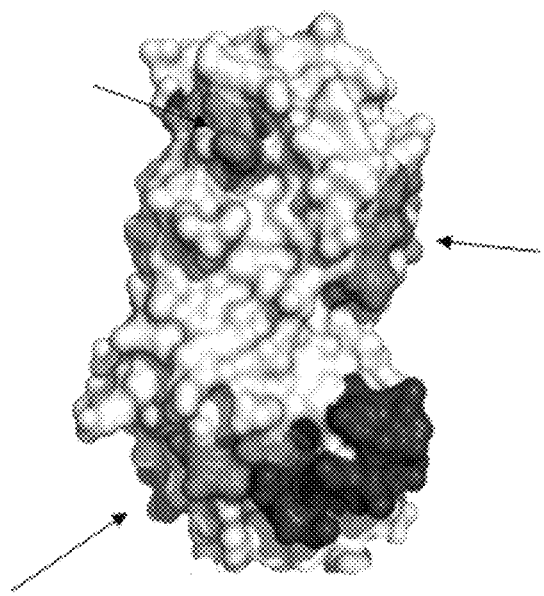
Figure 9B:
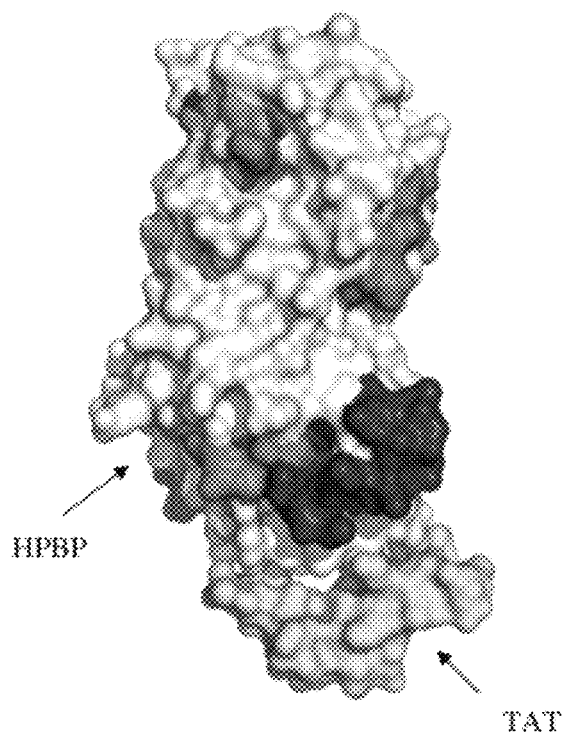

FIGS. 9A and 9B show the molecular modelling of the HPBP/Tat interaction.

FIG. 9A shows the three-dimensional structure of the HPBP protein indicating the epitopes recognized by the antibodies. The regions in dark grey ▓ located by arrows (→) represent the epitopes not interfering with the HPBP/Tat interaction, the region in black ▌ represents the zone of interaction with the Tat protein.

FIG. 9B shows the molecular modelling of the HPBP/Tat complex.

Figure 10:
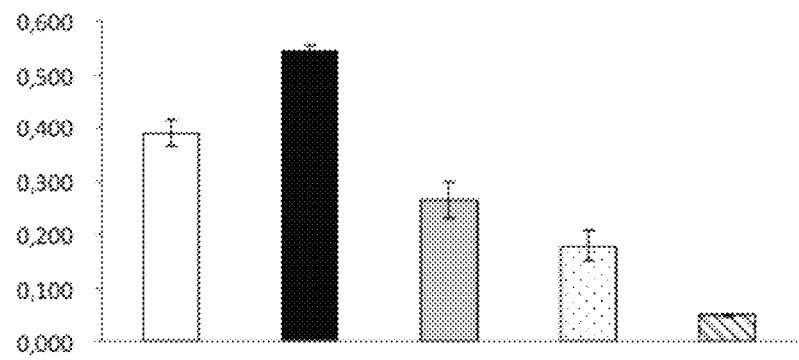

FIG. 10 shows histograms measuring the cell toxicity of the HPBP protein.

The white bar represents the untreated control cells, the black bar represents cells treated with the HPBP protein at a concentration of 0.2 µg·mL$^{-1}$, the grey bar represents cells treated with the HPBP protein at a concentration of 2 µg·mL$^{-1}$, the bar with dots represents cells treated with the HPBP protein at a concentration of 20 µg·mL$^{-1}$ and the hatched bar represents cells treated with the HPBP protein at a concentration of 0.2 µg·mL$^{-1}$. The x-axis represents the optical density measured at 570 nm.

Figure 11:
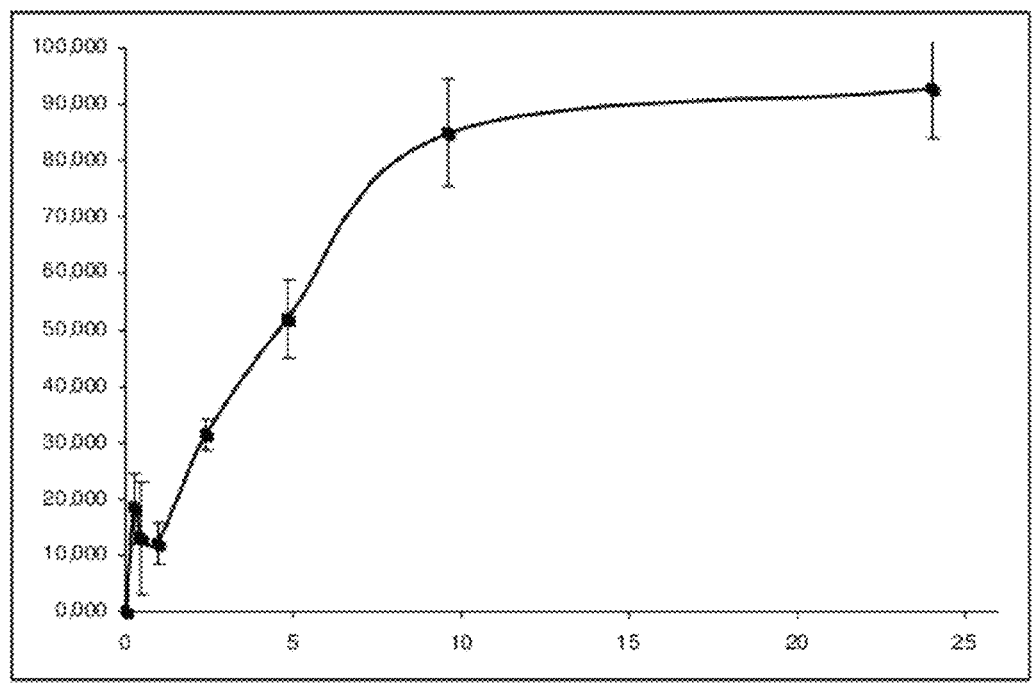

FIG. 11 shows a toxicity curve of the HPBP protein (expressed in %), as a function of the quantity of protein. This curve is obtained from lymphocyte cells originating from peripheral blood.

Figure 12:
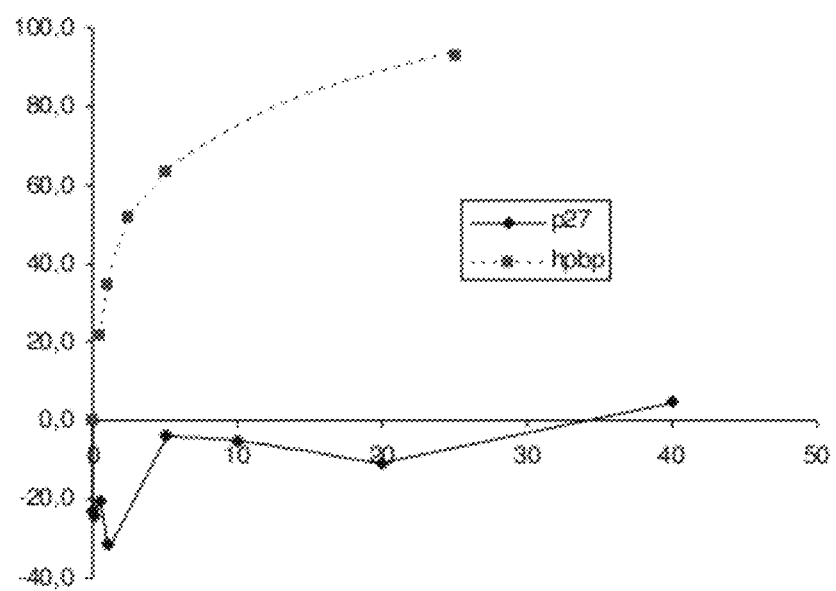

FIG. 12 shows a toxicity curve (expressed in %) of St. John's wort protein p27$^{SJ}$ (solid line) or of HPBP (dotted line), as a function of the quantity of protein. This curve is obtained from microglial cells.

EXPERIMENTAL PART

Unless otherwise indicated, all the experiments mentioned hereafter were carried out at least 3 times, independently.

Example 1

Purification of the HPBP Protein

Stage 1: Purification of the HPBP/PON-1 complex

The protein SEQ ID NO: 2 is purified from bags of frozen plasma (~200 mL) supplied by the Etablissement de Transfusion Sanguine of Lyon-Beynost. The fibrin clot, formed by the addition of 1M (1% v/v) of $CaCl_2$ to the plasma is separated from the serum by filtration. The serum is then mixed with 400 mL of affinity gel (Cibacron 3GA-Agarose, C-1535, Sigma) equilibrated with a buffer A (Tris/HCl 50 mM, $CaCl_2$ 1 mM, NaCl 4M, pH 8). Under these conditions, mainly the HDLs ("high density lipoproteins") are adsorbed. After incubation for 6 to 8 hours, the proteins not adsorbed on the gel are removed by filtration on frit of porosity No. 2. This washing is carried out until no more protein is detected in the eluate (UV absorption at 280 nm). The gel is then equilibrated with a buffer B (Tris/HCl 50 mM, $CaCl_2$ 1 mM, pH 8) then placed in an XK 50/30 column (Pharmacia). The elution is carried out by adding 1 g/l of sodium deoxycholate and 0.1% of triton X-100 to buffer B. The fractions showing an arylesterase activity are mixed and injected onto 50 mL of an anion-exchange gel (DEAE Sepharose Fast Flow, Pharmacia) arranged in an XK 26/70 column (Pharmacia) and equilibrated with buffer B and 0.1% of triton X-100. The elution is carried out by NaCl gradient. A first plateau is reached at 87.5 mM of NaCl in order to eliminate the apo A-I, a protein linked to paraoxonase, and the majority of the contaminating proteins. Human paraoxonase (PON1) is approximately eluted at a concentration of 140 mM of NaCl.

The HPBP protein co-purifies with the PON-1 protein.

Stage 2: Separation of the PON-1 and HPBP Proteins

The PON-1/HPBP complexes are separated on a hydroxyapatite column (AKTA FPLC system) (Amersham Biosciences) equipped with UNICORN software (version 3.2) for controlling the separation units. Chromatography is carried out at 25° C.).

The fractions of active proteins originating from the ion-exchange column are loaded onto a glass column (1 cm×10 cm, Amersham) containing 2 ml of Bio-Gel HTP hydroxyapatite resin at a flow rate of 0.5 mL/min.

The hydroxyapatite resin is equilibrated beforehand with a 10 mM sodium phosphate buffer, pH 7.0, with or without 0.1% Triton (Buffer A).

After washing with buffer A, the proteins are eluted in a linear manner by increasing the ionic strength of the sodium phosphate buffer from 10 to 400 mM (pH 7.0), or directly to 400 nM sodium phosphate buffer. The equilibration and the elution are carried out without calcium.

The PON-1 protein is eluted at a concentration of approximately 0.3 mg/mL, a concentration dependent on the initial human sample.

The HPBP protein is eluted at a concentration of approximately 0.05 mg/mL, a concentration dependent on the initial human sample.

The fractions collected are analyzed on SDS-PAGE gel with a polyacrylamide concentration of 10%. The proteins are separated for 35 min at constant voltage (200 V). The proteins, once separated are visualized by staining with silver nitrate (Silver Stain Plus kit, Bio-Rad).

Figure 1:
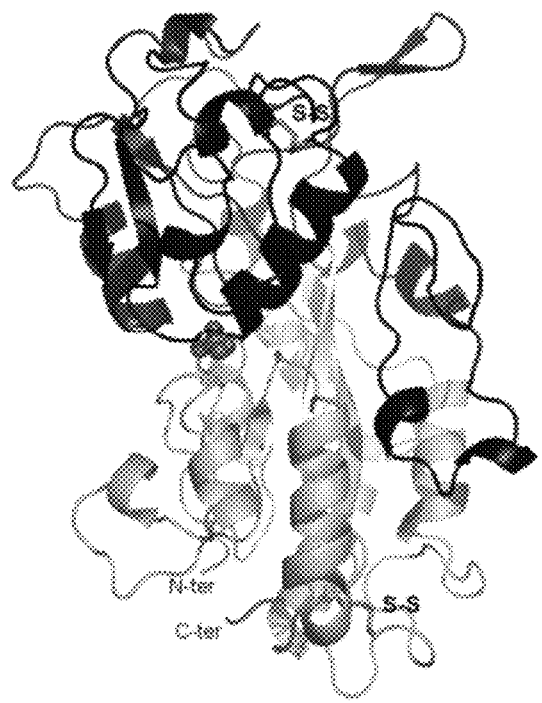
FIGS. 1 to 12 illustrate the invention.
Figure 2:
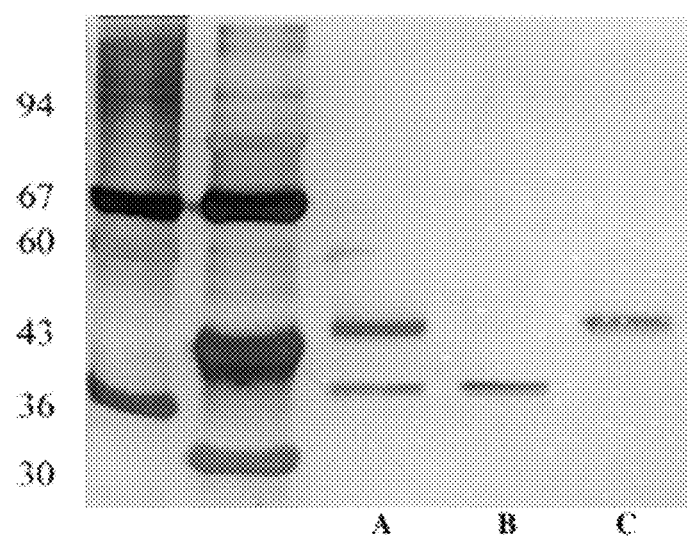

A separation gel of the isolated proteins is shown in FIG. 2.

Example 2

In Vitro Interaction of the HPBP and C/EBPβ Proteins

The combination of the Human Phosphate Binding Protein (HPBP) with the C/EBPβ protein is carried out using an ELISA technique.

In ELISA flat-bottom 96-well plates having a high binding affinity for proteins, the C/EBPβ protein is adsorbed on the support and incubated overnight at 4° C.

The proteins not bound to the plate are removed by washing with a Phosphate Buffered Saline (PBS) buffer containing 10 mg/mL of Bovine Serum Albumin (BSA).

The wells are saturated with a Phosphate Buffered Saline (PBS) buffer solution containing 20 mg/mL of Bovine Serum Albumin (BSA) for 1 hour at room temperature in order to remove the background noise.

After washing with a Phosphate Buffered Saline (PBS) solution containing 10 mg/mL of Bovine Serum Albumin (BSA), different solutions of pure HPBP from 0.1 nM to 100 mM are added to the wells for incubation for 1-3 hours at RT.

The plate is once again washed then incubated with mouse monoclonal anti-HPBP antibodies or rabbit polyclonal anti-HPBP antibodies for incubation for 1-3 hours at RT.

Finally, after a new washing, antibodies coupled to Horseradish Peroxidase (HRP) recognizing mouse or rabbit Fc fragments are added to the wells for incubation for 1-3 hours at RT.

Then after a last washing, the plate is incubated with an HRP substrate (3,3',5,5'-tetramethylbenzidine: TNB in the presence of hydrogen peroxide $H_2O_2$). The reaction is stopped after 10 minutes by adding $H_2SO_4$. The optical density of the product of the reaction is then measured with a spectrophotometer at 450 nm.

The results show that the HPBP protein and the C/EBPβ protein are capable of interacting in vitro.

Example 3

In Vivo Interaction of the HPBP and C/EBPβ or HPBP and Tat Proteins

In order to validate the interaction between HPBP and C/EBPβ, co-immunoprecipitation experiments were carried out.

Transformed human cell lines (Jurkat cells, HeLa cells etc.) or primary cells (circulating lymphocytes etc.) are incubated with a solution of HPBP protein.

The cells are then lysed and the HPBP protein is immunoprecipitated using specific antibodies, in a buffer making it possible to preserve the protein interactions.

The immunoprecipitated proteins are separated on gel according to the SDS-PAGE technique, the proteins are transferred to a nitrocellulose or PVDF membrane, and the presence of the C/EBPβ protein is revealed by the Western blot technique using specific antibodies directed against the C/EBPβ protein.

Similar experiments are carried out by immunoprecipitating the C/EBPβ protein and revealing the presence of the HPBP protein.

In order to validate the interaction between HPBP and Tat, co-immunoprecipitation experiments were carried out.

Transformed human cell lines (Jurkat cells, macrophage lines etc.) or primary cells (circulating lymphocytes etc.) infected with HIV, or expressing the recombinant Tat protein, are incubated with a solution of HPBP protein.

The cells are then lysed and the HPBP protein is immunoprecipitated using specific antibodies, in a buffer making it possible to preserve the protein interactions.

The immunoprecipitated proteins are separated on gel according to the SDS-PAGE technique, the proteins are transferred to a nitrocellulose or PVDF membrane, and the presence of the Tat protein is revealed by the Western-blot technique using specific antibodies directed against the Tat protein.

Similar experiments are carried out by immunoprecipitating the Tat protein and revealing the presence of the HPBP protein.

Example 4

HPBP Interferes with the C/EBPβ-Tat Interaction

The C/EBPβ-Tat interaction of HIV has been described by [Abraham et al. *J. Neuroimmunol.* 2005 March; 160(1-2): 219-27].

In order to measure the interference of the HPBP protein with the C/EBPβ-Tat interaction, an ELISA test was carried out.

In flat-bottom 96-well ELISA plates having a high protein-binding affinity the C/EBPβ protein is adsorbed on the support and incubated overnight at 4° C.

The proteins not bound to the plate are removed by washing with a Phosphate Buffered Saline (PBS) buffer containing 10 mg/mL of Bovine Serum Albumin (BSA).

The wells are saturated with a Phosphate Buffered Saline (PBS) buffer solution containing 20 mg/mL of Bovine Serum Albumin (BSA) for 1 hour at room temperature in order to eliminate the background noise.

After washing with a Phosphate Buffered Saline (PBS) solution, different solutions of pure HPBP from 0.1 nM to 100 mM are added to the wells for incubation for 1-3 hours at RT.

The plate is once again washed then incubated with TAT protein at different concentrations for 1-3 hours at room temperature.

The plate is once again washed then incubated with mouse monoclonal anti-TAT antibodies or rabbit polyclonal anti-TAT antibodies for a 1-3 hours' incubation at RT.

Finally, after a new washing, antibodies coupled to Horseradish Peroxydase (HRP) recognizing the mouse or rabbit Fc fragments are added to the wells for incubation for 1-3 hours at RT.

Then after a last washing, the plate is incubated with an HRP substrate (3,3',5,5'-tetramethylbenzidine: TNB in the presence of hydrogen peroxide $H_2O_2$). The reaction is stopped after 10 min by adding $H_2SO_4$. The optical density of the product of the reaction is then measured with a spectrophotometer at 450 nm.

Example 6

HPBP Inhibits the Replication and Inhibits the Transcription of the Genome of the HIV Virus Method: a Jurkat CD4+ T lymphocyte cell line (line 1G5) having integrated into its genome a construction comprising a luciferase reporter gene the expression of which is controlled by the HIV-1 promoter (HIV-1 LTR; HIV-LTR Jurkat line) was used. The measurement of luciferase activity from the cell extracts therefore makes it possible to estimate the HIV-1 transcriptional activity.

The Jurkat HIV-LTR and Jurkat 1G5 lines were transfected by means of the DEAE-dextran technique with the proviral genome NL4.3 (complete HIV-1 genome, strain LAI).

The HIV-LTR Jurkat and 1G5 Jurkat lines thus infected, are treated 24 hours later with HPBP/PON protein complexes or with purified PON or HPBP proteins at a final concentration of 2 µg/mL of medium (52 nM of protein alone).

The cells and the cell supernatant are sampled after treatment for 24 hours.

The transcriptional activity is measured by carrying out a luciferase test. The intensity of the HIV-1 replication is measured by means of ELISA assay of the quantity of viral p24 capsid proteins present in the supernatant of the cell cultures of the infected 1G5 lines [Rohr, O., et al. (2000). *The Journal of Biological Chemistry* 275, 2654-2660].

An untreated negative control as well as a positive control treated with AZT at a final concentration of 10 µM were carried out in parallel. Each experiment is carried out in triplicate.

In parallel, the infected lymphocyte lines obtained were treated with 10 µg of potato DING protein.

The results show that HPBP has a repressive effect on HIV-1 replication (FIG. 4) in the CD4+ T lymphocytes (89% inhibition). By contrast, PON-1 and HPBP, or PON-1 protein has no repressive effect. Moreover, a PON-1/HPBP mixture purified according to a standard protocol does not have inhibition properties as great as HPBP protein alone.

Inhibition of replication appears to pass through inhibition of transcriptional activity which is 80% repressed by HPBP (FIG. 3). In the same way as for the replicative activity, a mixture of the PON-1 and HPBP proteins, or the PON-1 protein alone does not have such an inhibiting effect.

Inhibition of HIV replication by the HPBP protein is significantly greater (89% inhibition) than that observed in the case of treatment with 10 µM of AZT (60% inhibition) (FIG. 6). Moreover, HPBP inhibits the viral replication by more than a factor of 6, whereas AZT has no effect on the replication of the virus (FIG. 5).

The anti-HIV activity of HPBP appears to pass through inhibition of the virus transcription stage. This stage of the viral cycle is not yet targeted by current therapeutic strategies. The virus strains resistant to the molecules used within the context of an active multi therapy (HAART) have therefore not been subjected to the selection pressure which makes it possible to provide any resistance to treatment with HPBP. The repressive efficacy observed for the HIV-1 strain NL4.3 should therefore logically be comparable for other virus strains including strains resistant to the therapies.

Experiments with potato DING protein show that, unexpectedly, the protein homologous to HPBP is not capable of inhibiting HIV replication, nor even of inhibiting HIV transcription. By contrast, the potato protein has more than 3 times the replication stimulating activity (FIG. 6) and more than 5 times the transcription stimulating activity (FIG. 5).

Example 7

HPBP Inhibits Expression of the Proinflammatory MCP-1 and IL-6 Genes

Transformed cell lines with constructions where the luciferase gene is brought under the control of the regulatory sequences of the MCP-1 gene or the IL-6 gene are treated or not treated with an inflammation inducer (LPS), and treated or not treated in parallel with HPBP protein.

The induction of the luciferase is revealed using the ad hoc substrate (for example luciferin), and the luciferase activity is measured using a luminometer.

Example 8

Dose-Response of HIV Inhibition by HPBP

The most effective concentration of HPBP protein (inhibitory concentration 50; $IC_{50}$) for inhibiting HIV-1 replication and transcription was evaluated according to the method described in Example 6.

The cells were treated with HPBP protein concentration ranges varying from 0.1 nM to 100 mM.

Example 9

In Vivo Measurement of the Toxicity of the Proteins

The toxicity of the HPBP protein is evaluated by measuring the proliferation and viability of Jurkat human cell lines treated with doses of HPBP varying from 0.1 nM to 100 mM.

The proliferation is measured by counting the cells daily, after staining with Trypan blue in order to exclude dead cells, or by staining with MTT (see below).

An alternative method consists of measuring the incorporation of tritiated thymidine ($^3$H) which provides evidence of DNA replication, and therefore of cell division.

The viability of these same cells can be estimated by different techniques, in particular the counting of Trypan blue-positive cells (cells having incorporated the stain). Other techniques for measuring apoptosis are also used such as measurement of the so-called "subG1" fragmented quantity of DNA by flow cytometry, or measurement of the early (Anexin V) or late (nucleosomal fragmentation of DNA) markers of apoptosis.

Example 10

Inhibition of HIV Strains Resistant to Standard Therapies

In France in 2003-2004, the frequency of viruses resistant to at least one antiretroviral in patients diagnosed at the time of their primary infection was 12.3%. The frequency of viruses resistant to the INTIs is 6%, to the INNTIs 5.9% and to the IPs 3.4%.

The resistance mechanisms and the mutations involved in the resistance to the antiretrovirals are essentially known for the HIV-1 isolates of sub-type B (6), which occur mostly in developed countries.

The inhibition by the HPBP protein of the viral replication and viral transcription of an AZT-resistant strain (proviral genome NL4.3) (complete HIV-1 genome, strain LAI) possessing the mutation T215Y was tested according to the protocol described in Example 6.

Example 11

Tests of the Action of HPBP on Other HIV-Infected Cells

Besides the T lymphocyte cells, HIV is capable of infecting the macrophage, dendritic and microglial cells.

The inhibition of the viral replication and viral transcription is evaluated as described in Example 6, using the following cells:
human macrophage THP-1 cells (ATCC No. TIB-202™), and
human microglial cells: HMO6 [Nagai A. et al. (2001) *Neurobiology of Disease* 8, 1057-1068].

Example 12

Assay of HPBP in Cohorts of Non-Progressive Patients

The concentration of HPBP in plasma protein was tested in non-progressive patients by means of an HPBP ELISA.

In flat-bottom 96-well ELISA plates having a high protein-binding affinity, anti-HPBP antibodies are adsorbed on the support and incubated overnight at 4° C.

The antibodies not bound to the plate are removed by washing with a Phosphate Buffered Saline (PBS) buffer containing 10 mg/mL of Bovine Serum Albumin (BSA).

The wells are saturated with a Phosphate Buffered Saline (PBS) buffer solution containing 20 mg/mL of Bovine Serum Albumin (BSA) for 1 hour at room temperature in order to eliminate the background noise.

After washing with a Phosphate Buffered Saline (PBS) solution containing 10 mg/mL of Bovine Serum Albumin (BSA), different dilutions of serum from patients are added to the wells for incubation for 1-3 hours at RT.

The plate is once again washed then incubated with mouse monoclonal anti-HPBP antibodies or rabbit anti-HPBP polyclonal antibodies for incubation for 1-3 hours at RT.

Finally, after a new washing, antibodies coupled to Horseradish Peroxydase (HRP) recognizing the mouse or rabbit Fc fragments are added to the wells for incubation for 1-3 hours at RT.

Then after a last washing, the plate is incubated with an HRP substrate (3,3',5,5'-tetramethylbenzidine: TNB in the presence of hydrogen peroxide $H_2O_2$). The reaction is stopped after 10 min by adding $H_2SO_4$. The optical density of the product of the reaction is then measured with a spectrophotometer at 450 nm.

ELISA makes it possible to determine the HPBP protein concentration in the patients' serum.

Example 13

In Vitro Interaction of the HPBP and Tat Proteins

The combination of the Human Phosphate Binding Protein (HPBP) with the C/EBPβ protein is carried out using an ELISA technique.

In flat-bottom 96-well ELISA plates having a high protein-binding affinity the GST-Tat protein is adsorbed on the support and incubated overnight at 4° C.

The proteins not bound to the plate are removed by washing with a Phosphate Buffered Saline (PBS) buffer containing 10 mg/mL of Bovine Serum Albumin (BSA).

The wells are saturated with a Phosphate Buffered Saline (PBS) buffer solution containing 20 mg/mL of Bovine Serum Albumin (BSA) for 1 hour at room temperature in order to eliminate the background noise.

After washing with a Phosphate Buffered Saline (PBS) solution containing 10 mg/mL of Bovine Serum Albumin (BSA), different solutions of pure HPBP from 0.1 nM to 100 mM are added to the wells for incubation for 1-3 hours at RT.

The plate is once again washed then incubated with mouse monoclonal anti-HPBP antibodies or rabbit anti-HPBP polyclonal antibodies for incubation for 1-3 hours at RT.

Finally, after a new washing, antibodies coupled to Horseradish Peroxydase (HRP) recognizing the mouse or rabbit Fc fragments are added to the wells for incubation for 1-3 hours at RT.

Then after a last washing, the plate is incubated with an HRP substrate (3,3',5,5'-tetramethylbenzidine: TNB in the presence of hydrogen peroxide $H_2O_2$). The reaction is stopped after 10 min by adding $H_2SO_4$. The optical density of the product of the reaction is then measured with a spectrophotometer at 450 nm.

The results show that the HPBP protein and the Tat protein are capable of interacting in vitro.

Example 14

In Vitro Interaction of HPBP and Tat Protein

Preliminary Preparation:

By immunization of rabbits and mice, the Inventors obtained monoclonal and polyclonal antibodies targeting the HPBP protein. The positions of the epitopes recognized by the monoclonal antibodies were characterized and located on the three-dimensional structure of HPBP. These molecular tools were used in order to carry out Western blot, immunohistochemical and ELISA studies. Knowing the position of the epitopes recognized by the different monoclonal antibodies led to the establishment of a system making it possible to quantify and map the interactions between HPBP and its partners.

Protocol:

The inventors used the Enzyme Linked Immunosorbent Assay (ELISA) technique, suited to studying the interaction between the HPBP protein and the HIV-1 (TAT) protein (Engvall and Perlmann, 1971)). The HIV-1 TAT protein was expressed in the form of a fusion with GST in order to obtain the soluble protein and in quantity (approximately 2 mg/mL).

The GST-TAT fusion protein, diluted to 1/250 in PBS (Biorad ref: 161-0780EDU) is bound by adsorption at the bottom of the wells of an ELISA plate (Greiner Bio-one Medium Binding 96 Well Plate MICROLON™200 Flat-Bottom Clear) leaving the plate at 4° C. overnight. The plate is then saturated with a Bovine Serum Albumin (BSA) solution at 20 mg/mL in order to eliminate the non-specific binding sites for 1 hour at room temperature then washed with PBS. Three dilutions of the HPBP protein (1 mg/mL, 0.5 mg/mL and 0.25 mg/mL) diluted in PBS/BSA to 10 mg/mL are then deposited in the wells for 3 hours at 37° C. The plate is then washed 3 times with PBS/BSA at 10 mg/mL in order to remove the non-bound proteins. In order to test a given epitope, the monoclonal antibody diluted to 1/1000 in PBS/BSA 10 mg/mL is deposited in the wells for 1 hour at 37° C. The plate is once again washed 3 times with PBS/BSA 10 mg/mL in order to remove the non-bound antibodies. A dilution of Horseradish Peroxydase anti-mouse secondary antibodies (Biorad ref: 170-5047) coupled to the diluates 1/2000 is then deposited in the wells in order to reveal the interaction for 1 hour at 37° C. Finally, the plate is washed 3 times with PBS/BSA 10 mg/mL then once by PBS and revealed using a chromogenic substrate (3,3',5,5'-tetramethylbenzidine (TMB), Biorad ref: 166-2402) which reveals the interaction.

By testing the binding capacities of the different monoclonal antibodies, it is possible to demonstrate epitopes which are no longer recognized. These epitopes are masked by the formation of the DING protein-target protein complex. By identifying the antibodies which no longer recognize the complex, we can model on the structure of HPBP the zone responsible for the interaction.

The regions recognized by the antibodies are shown in FIG. 9A.

For the purpose of achieving molecular visualization of the interaction in the absence of crystallographic data, the Inventors made use of modelling by molecular docking. In order to model the interaction between the HPBP model DING protein and the TAT protein, the Inventors used the structure of the TAT protein which seems the most accurate (Anand et al., 2008, Nat Struct Mol Biol 15, 1287-1292). The docking was carried out using PATCHDOCK software (Schneidman-Duhovny et al., 2005, Nucleic Acids Res 33, W363-367), and the best 100 solutions obtained were then entered into the FIREDOCK software (Mashiach et al., 2008, Nucleic Acids Res 36, W229-232) which makes it possible to refine the results by releasing the side chains. We then obtained the best 10 solutions which were classified in terms of overall energy and visualized with pymol 1.1. The most favourable solution in terms of overall energy, also contrasted with the other solutions, is in accordance with the experimental mapping data.

The modelling of the HPBP/Tat interaction is shown in FIG. 9B.

The following table summarizes the interaction data, specifying the epitopes of the HPBP protein necessary for the interaction with the Tat protein

| Pharmacophore Sequences | Mapping data | Interaction data (Docking) |
|---|---|---|
| 1-6 | DINGGG | |
| 47-57 | FGTDTTKNVHW | |
| 78-80 | | PGW |
| 308-311 | | ANAT |
| 356-361 | TASNAL | |
| 370-376 | | GGKGRPE |

Thus a protein capable of interacting with the Tat protein is the following:

The dashes (-) represent any one of the 20 natural amino acids known from the state of the art, or optionally modified amino acids.

In other words, the amino acids represented by a letter are the amino acids essential for the interaction. Also, any variant of HPBP possessing at least 72% homology, or identity, with the protein of sequence SEQ ID NO: 1, 2 or 3, will retain its properties of interaction with Tat if the amino acids indicated are present.

Example 15

Toxicity of the HPBP Protein

The cell toxicity of the HPBP protein was measured on cells in culture.
Cell Line R3HR-1G5 (1g5)

$5.10^6$ cells/mL of the lymphoid line B 1g5 were seeded on plates and treated, or not treated, with different doses of purified HPBP protein: 0.2 µg/mL, 2 µg/mL, 20 µg/mL, or 90 µg/mL.

The cells are cultured for 24 hours at 37° C.

After culture for 24 hours, the toxicity of the protein is evaluated by measuring the number of living cells by the MTT method (3-(4,5-dimethylthiazol-2-yl)-2,5-diphenyl tetrazolium bromide) as described in Berridge et al. Biotechnology Annual Review, 2005, 11, 127-152.

Briefly, 10 µL of MTT is added to each culture.

The mixture is added quickly over 1 minute, then the cultures are returned to 37° C. for 4 hours.

The culture supernatant is then aspirated, and the crystals formed by the presence of MTT are dissolved with acetic acid.

The optical density (OD) of each of the cultures is measured at 570 nm using a spectrophotometer.

The results obtained are presented in FIG. 10.

The results show that the lethal dose 50% (LD50—Dose killing half of the cells) is approximately 20 µg/mL, which corresponds to a dose 10 to 100 times greater than the dose necessary to inhibit HIV.
Peripheral Blood Lymphocyte (PBL) Cells Similar experiments were carried out on primary lymphocytes. Conditions similar to those used for the 1g5 cells were used.

The PBL cells were treated with 0.24 µg/mL, 0.48 µg/mL, 0.96 µg/mL, 2.4 µg/mL, 4.8 µg/mL, 9.6 µg/mL, or 24 µg/mL of HPBP protein. Untreated cells were tested as a control.

The results are presented in FIG. 11.

The results show that the LD50 is approximately 5 µg/mL.
Microglial Cell Line

Similar experiments were carried out on microglial lines. Conditions similar to those used for the 1g5 cells were used, with $5.10^5$ cells/mL.

```
  1 DINGGG---- ---------- ---------- ---------- ------FGTD TTKNVHW---  60

61 ---------- -------PGW ---------- ---------- ---------- ---------- 120

121 ---------- ---------- ---------- ---------- ---------- ---------- 180

181 ---------- ---------- ---------- ---------- ---------- ---------- 240

241 ---------- ---------- ---------- ---------- ---------- ---------- 300

301 -------ANA T--------- ---------- ---------- ---------- -----TASNA 360

361 L--------G GKGRPE                                                  376
```

The PBL cells were treated with 0.24 μg/mL, 0.48 μg/mL, 0.96 μg/mL, 2.4 μg/mL, 4.8 μg/mL, 9.6 μg/mL, or 24 μg/mL of HPBP protein. Untreated cells were tested as a control.

The results are presented in FIG. 12, dotted curve.

The results show that the LD50 is approximately 2.5 μg/mL.

Example 16

Toxicity of the p27SJ Protein

The cell toxicity of St. John's wort protein p27$^{SJ}$ was measured on cells in culture under the conditions described in Example 15. The p27$^{SJ}$ was tested at doses of 0 μg/mL (control), 0.01 μg/mL, 0.1 μg/mL, 0.5 μg/mL, 1 μg/mL, 5 μg/mL, 10 μg/mL, 20 μg/mL and 40 μg/mL.

The results expressed as a percentage of toxicity are presented in FIG. 12, solid curve.

The results show that the LD50 is clearly greater than 2.5 μg/mL (LD50 HPBP), since at a dose of 40 μg/mL of p27$^{SJ}$, only approximately 4% of the cells are dead. Thus the p27$^{SJ}$ protein has a toxicity very clearly less than that of the HPBP protein.

Results comparable to those obtained for the p27$^{SJ}$ protein were obtained with potato DING protein.

Examples 17

Combined Effect of HPBP+Antiviral Agents

Method: a Jurkat CD4+ T lymphocyte cell line (line 1G5) having integrated into its genome a construction comprising a luciferase reporter gene the expression of which is controlled by the HIV-1 promoter (HIV-1 LTR; HIV-LTR Jurkat line) was used. Measurement of luciferase activity from the cell extracts therefore makes it possible to estimate the HIV-1 transcriptional activity.

The HIV-LTR Jurkat and 1G5 Jurkat lines were transfected by means of the DEAE-dextran technique with the proviral genome NL4.3 (complete HIV-1 genome, strain LAI).

The thus-infected HIV-LTR Jurkat and Jurkat 1G5 lines are treated 24 hours later with the HPBP at a final concentration of 2 μg/mL of medium (52 nM of protein alone) or HPBP 2 μg/mL+10 μM AZT or AZT alone. The cells and the cell supernatant are sampled after treatment for 24 hour.

The transcriptional activity and inhibition of the replication are measured as described in Example 6.

The results indicate that the HPBP+AZT combination has a better effect on the transcriptional activity and inhibition of the replication.

Similar results are obtained with HPBP+reverse transcriptase inhibitor, HPBP+entry inhibitor, HPBP+fusion inhibitor or HPBP+integrase inhibitor combinations.

The invention claimed is:

1. A method of inhibiting replication of a virus, comprising administering to a patient in need thereof a composition comprising an effective amount of a protein in combination with a pharmaceutically acceptable vehicle, wherein said protein comprises the amino acid sequence selected from the group consisting of:
SEQ ID NO: 5, SEQ ID NO: 6, SEQ ID NO: 1, an amino acid sequence exhibiting at least 90% homology with SEQ ID NO: 5, an amino acid sequence exhibiting at least 90% homology with SEQ ID NO: 6, and an amino acid sequence exhibiting at least 90% homology with SEQ ID NO: 1,
wherein said protein interacts with at least one of transcription factor C/EBPβ and viral protein Tat by a direct, chemical, electrostatic or ionic bond, and
said virus is a virus that requires the transcription factor C/EBPβ for gene transcription.

2. The method according to claim 1, wherein said protein consists of the amino acid sequence selected from the group consisting of: SEQ ID NO: 7, SEQ ID NO: 9, SEQ ID NO: 6, SEQ ID NO: 8, SEQ ID NO: 10, SEQ ID NO: 1, SEQ ID NO: 2 and SEQ ID NO: 3.

3. The method according to claim 1, wherein said virus is selected from the group consisting of: HIV viruses, hepatitis viruses, and herpes viruses.

4. The method according to claim 3, wherein said HIV viruses are HIV-1 or HIV-2 viruses.

5. The method according to claim 1, wherein the composition is administered to the subject at a dose of from 0.1 nM to 10 μM.

6. The method according to claim 1, further comprising administering to the patient at least one additional compound possessing antiviral properties and/or at least one compound possessing anti-inflammatory properties.

7. The method according to claim 6, wherein said additional antiviral compound is a protease inhibitor or a reverse transcriptase inhibitor.

8. The method according to claim 6, wherein said composition and said additional antiviral compound are administered simultaneously, separately, or spread over time.

9. The method according to claim 1, wherein said patient is suffering from one or more of rheumatoid arthritis, auto-immune disease, lupus, disseminated erythematous lupus, food allergies, allergies of the respiratory tract, pollen allergies, Sjögren's syndrome, scleroderma, dermatomyositis, polymyositis, polymyalgia rheumatica, osteoarthritis, or septic arthritis.

10. The method according to claim 7, wherein the protease inhibitor is selected from the group consisting of ritonavir, indinavir, saquinavir and nelfinavir.

11. The method according to claim 7, wherein the reverse transcriptase inhibitor is selected from the group consisting of AZT, ddI, ddC, 3TC, d4T, nevirapine, delavirdine and efavirenz.

12. The method according to claim 1, wherein the composition is administered to the subject at a dose of from 10 nM to 100 nM.

13. The method according to claim 1, wherein the composition is administered to the subject at a dose of from 30 nM to 70 nM.

* * * * *